(12) United States Patent
Cohen

(10) Patent No.: US 10,517,530 B2
(45) Date of Patent: Dec. 31, 2019

(54) METHODS AND DEVICES FOR DELIVERING AND MONITORING OF TOBACCO, NICOTINE, OR OTHER SUBSTANCES

(71) Applicant: Juul Labs, Inc., San Francisco, CA (US)

(72) Inventor: Gal A. Cohen, San Francisco, CA (US)

(73) Assignee: Juul Labs, Inc., San Francisco, CA (US)

( * ) Notice: Subject to any disclaimer, the term of this patent is extended or adjusted under 35 U.S.C. 154(b) by 973 days.

(21) Appl. No.: 14/461,284

(22) Filed: Aug. 15, 2014

(65) Prior Publication Data
US 2014/0378790 A1    Dec. 25, 2014

Related U.S. Application Data

(63) Continuation-in-part of application No. 14/012,952, filed on Aug. 28, 2013, now abandoned.
(Continued)

(51) Int. Cl.
| | |
|---|---|
| *A61B 5/00* | (2006.01) |
| *A24F 47/00* | (2006.01) |
| *A61B 5/145* | (2006.01) |
| *G01N 33/00* | (2006.01) |
| *G01N 33/497* | (2006.01) |
| *A61B 5/08* | (2006.01) |

(52) U.S. Cl.
CPC ............ *A61B 5/486* (2013.01); *A24F 47/002* (2013.01); *A24F 47/008* (2013.01); *A61B 5/082* (2013.01); *A61B 5/14507* (2013.01); *A61B 5/14546* (2013.01); *G01N 33/497* (2013.01); *G01N 2033/4975* (2013.01)

(58) Field of Classification Search
CPC ................. A24F 47/002; A24F 47/008; G01N 2033/4975; G01N 33/497; A61B 5/082; A61B 5/14507; A61B 5/14546; A61B 5/486
See application file for complete search history.

(56) References Cited

U.S. PATENT DOCUMENTS

| | | |
|---|---|---|
| 374,584 A | 12/1887 | Cook |
| 576,653 A | 2/1897 | Bowlby |
| (Continued) | | |

FOREIGN PATENT DOCUMENTS

| | | |
|---|---|---|
| CA | 2641869 A1 | 5/2010 |
| CN | 85106876 A | 9/1986 |
| (Continued) | | |

OTHER PUBLICATIONS

Bradley et al.; Electronic cigarette aerosol particle size distribution measurements; Inhal. Toxicol.; 24(14); pp. 976-984; Dec. 2012.
(Continued)

*Primary Examiner* — Jennifer Wecker
(74) *Attorney, Agent, or Firm* — Mintz, Levin, Cohn, Ferris, Glovsky and Popeo, P.C.

(57) ABSTRACT

Methods, systems, and devices are described for providing risk evaluation and mitigation strategies for use with modified risk products or other tobacco products, and in particular, associated with nicotine and tobacco products.

18 Claims, 13 Drawing Sheets

Related U.S. Application Data

(60) Provisional application No. 61/694,046, filed on Aug. 28, 2012.

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempel |
| 2,327,120 A | 8/1943 | McCoon |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Jakob |
| 2,860,638 A | 11/1958 | Frank |
| 2,897,958 A | 8/1959 | Tarleton et al. |
| 2,935,987 A | 5/1960 | Ackerbauer |
| 3,146,937 A | 9/1964 | Joseph |
| 3,258,015 A | 6/1966 | Ellis et al. |
| 3,271,719 A | 9/1966 | Ovshinsky |
| 3,292,634 A | 12/1966 | Beucler |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Gottelman |
| 3,861,523 A | 1/1975 | Fountain et al. |
| 3,941,300 A | 3/1976 | Troth |
| 4,020,853 A | 5/1977 | Nuttall |
| 4,049,005 A | 9/1977 | Hernandez et al. |
| 4,066,088 A | 1/1978 | Ensor |
| 4,207,976 A | 6/1980 | Herman |
| 4,215,708 A | 8/1980 | Bron |
| 4,219,032 A | 8/1980 | Tabatznik et al. |
| 4,303,083 A | 12/1981 | Burruss |
| 4,506,683 A | 3/1985 | Cantrell et al. |
| 4,519,319 A | 5/1985 | Howlett |
| 4,520,938 A | 6/1985 | Finke |
| 4,595,024 A | 6/1986 | Greene et al. |
| 4,648,393 A | 3/1987 | Landis et al. |
| 4,708,151 A | 11/1987 | Shelar |
| 4,735,217 A | 4/1988 | Gerth et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,813,536 A | 3/1989 | Willis |
| 4,819,665 A | 4/1989 | Roberts et al. |
| 4,830,028 A | 5/1989 | Lawson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| 4,893,639 A | 1/1990 | White |
| 4,907,606 A | 3/1990 | Lilja et al. |
| 4,941,483 A | 7/1990 | Ridings et al. |
| 4,944,317 A | 7/1990 | Thal |
| 4,947,874 A | 8/1990 | Brooks et al. |
| 4,947,875 A | 8/1990 | Brooks et al. |
| 5,005,759 A | 4/1991 | Bouche |
| 5,020,548 A | 6/1991 | Farrier et al. |
| 5,027,836 A | 7/1991 | Shannon et al. |
| 5,031,646 A | 7/1991 | Lippiello et al. |
| 5,040,551 A | 8/1991 | Schlatter et al. |
| 5,050,621 A | 9/1991 | Creighton et al. |
| 5,060,671 A | 10/1991 | Counts et al. |
| 5,065,776 A | 11/1991 | Lawson et al. |
| 5,076,297 A | 12/1991 | Farrier et al. |
| 5,105,831 A | 4/1992 | Banerjee et al. |
| 5,105,838 A | 4/1992 | White et al. |
| 5,123,530 A | 6/1992 | Lee |
| 5,133,368 A | 7/1992 | Neumann et al. |
| 5,144,962 A | 9/1992 | Counts et al. |
| 5,152,456 A | 10/1992 | Ross et al. |
| 5,183,062 A | 2/1993 | Clearman et al. |
| 5,224,498 A | 7/1993 | Deevi et al. |
| 5,240,012 A | 8/1993 | Ehrman et al. |
| 5,249,586 A | 10/1993 | Morgan et al. |
| 5,261,424 A | 11/1993 | Sprinkel, Jr. |
| 5,269,237 A | 12/1993 | Baker et al. |
| 5,269,327 A | 12/1993 | Counts et al. |
| 5,303,720 A | 4/1994 | Banerjee et al. |
| 5,322,075 A | 6/1994 | Deevi et al. |
| 5,324,498 A | 6/1994 | Streusand et al. |
| 5,372,148 A | 12/1994 | McCafferty et al. |
| 5,388,574 A | 2/1995 | Ingebrethsen |
| 5,449,078 A | 9/1995 | Akers |
| 5,456,269 A | 10/1995 | Kollasch |
| 5,497,791 A | 3/1996 | Bowen et al. |
| 5,529,078 A | 6/1996 | Rehder et al. |
| 5,579,934 A | 12/1996 | Buono |
| 5,591,368 A | 1/1997 | Fleischhauer et al. |
| 5,605,226 A | 2/1997 | Hernlein |
| 5,641,064 A | 6/1997 | Goserud |
| 5,649,552 A | 7/1997 | Cho et al. |
| 5,666,977 A | 9/1997 | Higgins et al. |
| 5,666,978 A | 9/1997 | Counts et al. |
| 5,708,258 A | 1/1998 | Counts et al. |
| 5,730,118 A | 3/1998 | Hermanson |
| 5,730,158 A | 3/1998 | Collins et al. |
| 5,746,587 A | 5/1998 | Racine et al. |
| 5,810,164 A | 9/1998 | Rennecamp |
| 5,819,756 A | 10/1998 | Mielordt |
| 5,845,649 A | 12/1998 | Saito et al. |
| 5,865,185 A | 2/1999 | Collins et al. |
| 5,881,884 A | 3/1999 | Podosek |
| 5,931,828 A | 8/1999 | Durkee |
| 5,934,289 A | 8/1999 | Watkins et al. |
| 5,938,018 A | 8/1999 | Keaveney et al. |
| 5,944,025 A | 8/1999 | Cook et al. |
| 5,954,979 A | 9/1999 | Counts et al. |
| 5,967,310 A | 10/1999 | Hill |
| 5,975,415 A | 11/1999 | Zehnal |
| 5,979,460 A | 11/1999 | Matsumura |
| 5,994,025 A | 11/1999 | Iwasa et al. |
| 5,996,589 A | 12/1999 | St. Charles |
| 6,053,176 A | 4/2000 | Adams et al. |
| 6,089,857 A | 7/2000 | Matsuura et al. |
| 6,095,153 A | 8/2000 | Kessler et al. |
| 6,102,036 A | 8/2000 | Slutsky et al. |
| 6,125,853 A | 10/2000 | Susa et al. |
| 6,155,268 A | 12/2000 | Takeuchi |
| 6,164,287 A | 12/2000 | White |
| 6,196,232 B1 | 3/2001 | Chkadua |
| 6,234,169 B1 | 5/2001 | Bulbrook et al. |
| 6,269,966 B1 | 8/2001 | Pallo et al. |
| 6,324,261 B1 | 11/2001 | Merte |
| 6,349,728 B1 | 2/2002 | Pham |
| 6,381,739 B1 | 4/2002 | Breternitz, Jr. et al. |
| 6,386,371 B1 | 5/2002 | Parsons |

(56) References Cited

U.S. PATENT DOCUMENTS

| | | |
|---|---|---|
| 6,431,363 B1 | 8/2002 | Hacker |
| 6,446,793 B1 | 9/2002 | Layshock |
| 6,510,982 B2 | 1/2003 | White et al. |
| 6,532,965 B1 | 3/2003 | Abhulimen et al. |
| 6,536,442 B2 | 3/2003 | St. Charles et al. |
| 6,557,708 B2 | 5/2003 | Polacco |
| 6,598,607 B2 | 7/2003 | Adiga et al. |
| 6,603,924 B2 | 8/2003 | Brown et al. |
| 6,606,998 B1 | 8/2003 | Gold |
| 6,612,404 B2 | 9/2003 | Sweet et al. |
| 6,615,840 B1 | 9/2003 | Fournier et al. |
| 6,622,867 B2 | 9/2003 | Menceles |
| 6,655,379 B2 | 12/2003 | Clark et al. |
| 6,672,762 B1 | 1/2004 | Faircloth et al. |
| 6,688,313 B2 | 2/2004 | Wrenn et al. |
| 6,726,006 B1 | 4/2004 | Funderburk et al. |
| 6,772,756 B2 | 8/2004 | Shayan |
| 6,799,576 B2 | 10/2004 | Farr |
| 6,803,545 B2 | 10/2004 | Blake et al. |
| 6,805,545 B2 | 10/2004 | Slaboden |
| 6,810,883 B2 | 11/2004 | Felter et al. |
| 6,827,573 B2 | 12/2004 | St. Charles et al. |
| 6,954,979 B2 | 10/2005 | Logan |
| 7,000,775 B2 | 2/2006 | Gelardi et al. |
| 7,015,796 B2 | 3/2006 | Snyder |
| 7,488,171 B2 | 2/2009 | St. Charles et al. |
| D590,990 S | 4/2009 | Hon |
| D590,991 S | 4/2009 | Hon |
| 7,546,703 B2 | 6/2009 | Johnske et al. |
| 7,621,403 B2 | 11/2009 | Althoff et al. |
| 7,644,823 B2 | 1/2010 | Gelardi et al. |
| 7,767,698 B2 | 8/2010 | Warchol et al. |
| D624,238 S | 9/2010 | Turner |
| 7,801,573 B2 | 9/2010 | Yazdi et al. |
| 7,815,332 B1 | 10/2010 | Smith |
| 7,832,410 B2 | 11/2010 | Hon |
| 7,886,507 B2 | 2/2011 | McGuinness, Jr. |
| D642,330 S | 7/2011 | Turner |
| D644,375 S | 8/2011 | Zhou |
| 7,988,034 B2 | 8/2011 | Pezzoli |
| D653,803 S | 2/2012 | Timmermans |
| 8,141,701 B2 | 3/2012 | Hodges |
| 8,156,944 B2 | 4/2012 | Hon |
| 8,251,060 B2 | 8/2012 | White et al. |
| 8,322,350 B2 | 12/2012 | Lipowicz |
| 8,371,310 B2 | 2/2013 | Brenneise |
| 8,381,739 B2 | 2/2013 | Gonda |
| 8,387,612 B2 | 3/2013 | Damani et al. |
| 8,443,534 B2 | 5/2013 | Goodfellow et al. |
| 8,490,629 B1 | 7/2013 | Shenassa et al. |
| 8,511,318 B2 | 8/2013 | Hon |
| 8,539,959 B1 | 9/2013 | Scatterday |
| 8,541,401 B2 | 9/2013 | Mishra et al. |
| D691,324 S | 10/2013 | Saliman |
| D695,450 S | 12/2013 | Benassayag et al. |
| 8,596,460 B2 | 12/2013 | Scatterday |
| 8,671,952 B2 | 3/2014 | Winterson et al. |
| D707,389 S | 6/2014 | Liu |
| 8,741,348 B2 | 6/2014 | Hansson et al. |
| 8,809,261 B2 | 8/2014 | Elsohly et al. |
| 8,820,330 B2 | 9/2014 | Bellinger et al. |
| 8,851,081 B2 | 10/2014 | Fernando et al. |
| 8,881,737 B2 | 11/2014 | Collett et al. |
| 8,915,254 B2 | 12/2014 | Monsees et al. |
| 8,925,555 B2 | 1/2015 | Monsees et al. |
| D725,310 S | 3/2015 | Eksouzian |
| 8,991,402 B2 | 3/2015 | Bowen et al. |
| 9,095,175 B2 | 8/2015 | Terry et al. |
| 9,215,895 B2 | 12/2015 | Bowen et al. |
| 9,220,302 B2 | 12/2015 | DePiano et al. |
| 9,226,526 B2 | 1/2016 | Liu |
| 9,271,525 B2 | 3/2016 | Liu |
| 9,271,529 B2 | 3/2016 | Alima |
| 9,272,103 B2 | 3/2016 | Storz |
| 9,277,769 B2 | 3/2016 | Liu |
| 9,282,772 B2 | 3/2016 | Tucker et al. |
| 9,282,773 B2 | 3/2016 | Greim et al. |
| 9,289,014 B2 | 3/2016 | Tucker et al. |
| 9,308,336 B2 | 4/2016 | Newton |
| 9,326,547 B2 | 5/2016 | Tucker et al. |
| 9,351,522 B2 | 5/2016 | Safari |
| 10,111,467 B1* | 10/2018 | Arnel ............... H05B 1/0227 |
| 2001/0015209 A1 | 8/2001 | Zielke |
| 2001/0032643 A1 | 10/2001 | Hochrainer et al. |
| 2001/0032795 A1 | 10/2001 | Weinstein et al. |
| 2001/0052480 A1 | 12/2001 | Kawaguchi et al. |
| 2002/0078951 A1 | 6/2002 | Nichols et al. |
| 2002/0142291 A1 | 10/2002 | Bauer et al. |
| 2002/0175164 A1 | 11/2002 | Dees et al. |
| 2003/0004426 A1* | 1/2003 | Melker ............... G01N 29/022 |
| | | 600/532 |
| 2003/0005926 A1 | 1/2003 | Jones et al. |
| 2003/0089377 A1 | 5/2003 | Hajaligol et al. |
| 2003/0149372 A1* | 8/2003 | Smith ............... A61B 5/083 |
| | | 600/532 |
| 2004/0031495 A1 | 2/2004 | Steinberg |
| 2004/0050382 A1 | 3/2004 | Goodchild |
| 2004/0099266 A1 | 5/2004 | Cross et al. |
| 2004/0149296 A1 | 8/2004 | Rostami et al. |
| 2004/0149624 A1 | 8/2004 | Wischusen et al. |
| 2004/0173229 A1 | 9/2004 | Crooks et al. |
| 2004/0182403 A1 | 9/2004 | Andersson et al. |
| 2004/0221857 A1 | 11/2004 | Dominguez |
| 2004/0237974 A1 | 12/2004 | Min |
| 2005/0016549 A1 | 1/2005 | Banerjee et al. |
| 2005/0016550 A1 | 1/2005 | Katase |
| 2005/0034723 A1 | 2/2005 | Bennett et al. |
| 2005/0061759 A1 | 3/2005 | Doucette |
| 2005/0081601 A1* | 4/2005 | Lawson ............... G01N 33/497 |
| | | 73/23.3 |
| 2005/0118545 A1 | 6/2005 | Wong |
| 2005/0145533 A1 | 7/2005 | Seligson |
| 2005/0172976 A1 | 8/2005 | Newman et al. |
| 2005/0236006 A1 | 10/2005 | Cowan |
| 2005/0244521 A1 | 11/2005 | Strickland et al. |
| 2005/0268911 A1 | 12/2005 | Cross et al. |
| 2006/0018840 A1 | 1/2006 | Lechuga Ballesteros et al. |
| 2006/0054676 A1 | 3/2006 | Wischusen |
| 2006/0102175 A1 | 5/2006 | Nelson |
| 2006/0150991 A1 | 7/2006 | Lee |
| 2006/0191546 A1 | 8/2006 | Takano et al. |
| 2006/0191548 A1 | 8/2006 | Strickland et al. |
| 2006/0254948 A1 | 11/2006 | Herbert et al. |
| 2006/0255105 A1 | 11/2006 | Sweet |
| 2007/0006889 A1 | 1/2007 | Kobal et al. |
| 2007/0045288 A1 | 3/2007 | Nelson |
| 2007/0062548 A1 | 3/2007 | Horstmann et al. |
| 2007/0074734 A1 | 4/2007 | Braunshteyn et al. |
| 2007/0098148 A1 | 5/2007 | Sherman |
| 2007/0102013 A1 | 5/2007 | Adams et al. |
| 2007/0144514 A1 | 6/2007 | Yeates et al. |
| 2007/0163610 A1 | 7/2007 | Lindell et al. |
| 2007/0215164 A1 | 9/2007 | Mehio |
| 2007/0235046 A1 | 10/2007 | Gedevanishvili |
| 2007/0267033 A1 | 11/2007 | Mishra et al. |
| 2007/0277816 A1 | 12/2007 | Morrison et al. |
| 2007/0280652 A1 | 12/2007 | Williams |
| 2007/0283972 A1 | 12/2007 | Monsees et al. |
| 2008/0000763 A1 | 1/2008 | Cove |
| 2008/0023003 A1 | 1/2008 | Rosenthal |
| 2008/0029095 A1 | 2/2008 | Esser |
| 2008/0092912 A1 | 4/2008 | Robinson et al. |
| 2008/0138423 A1* | 6/2008 | Gonda ............... A24F 47/002 |
| | | 424/489 |
| 2008/0149118 A1 | 6/2008 | Oglesby et al. |
| 2008/0216828 A1 | 9/2008 | Wensley et al. |
| 2008/0241255 A1 | 10/2008 | Rose et al. |
| 2008/0257367 A1 | 10/2008 | Paterno et al. |
| 2008/0276947 A1 | 11/2008 | Martzel |
| 2009/0004249 A1 | 1/2009 | Gonda |
| 2009/0095287 A1 | 4/2009 | Emarlou |
| 2009/0111287 A1 | 4/2009 | Lindberg et al. |
| 2009/0126745 A1 | 5/2009 | Hon |
| 2009/0133691 A1 | 5/2009 | Yamada et al. |

(56) References Cited

U.S. PATENT DOCUMENTS

| | | |
|---|---|---|
| 2009/0230117 A1 | 9/2009 | Fernando et al. |
| 2009/0255534 A1 | 10/2009 | Paterno |
| 2009/0267252 A1 | 10/2009 | Ikeyama |
| 2009/0272379 A1 | 11/2009 | Thorens et al. |
| 2009/0283103 A1 | 11/2009 | Nielsen et al. |
| 2009/0288668 A1 | 11/2009 | Inagaki |
| 2009/0288669 A1 | 11/2009 | Hutchens |
| 2009/0293892 A1 | 12/2009 | Williams et al. |
| 2009/0293895 A1 | 12/2009 | Axelsson et al. |
| 2010/0000672 A1 | 1/2010 | Fogle |
| 2010/0006092 A1 | 1/2010 | Hale et al. |
| 2010/0024834 A1 | 2/2010 | Oglesby et al. |
| 2010/0031968 A1 | 2/2010 | Sheikh et al. |
| 2010/0156193 A1 | 6/2010 | Rhodes et al. |
| 2010/0163063 A1 | 7/2010 | Fernando et al. |
| 2010/0186757 A1 | 7/2010 | Crooks et al. |
| 2010/0200008 A1 | 8/2010 | Taieb |
| 2010/0236562 A1 | 9/2010 | Hearn et al. |
| 2010/0242974 A1 | 9/2010 | Pan |
| 2010/0242976 A1 | 9/2010 | Katayama et al. |
| 2010/0275938 A1 | 11/2010 | Roth et al. |
| 2010/0276333 A1 | 11/2010 | Couture |
| 2010/0307116 A1 | 12/2010 | Fisher |
| 2011/0030706 A1 | 2/2011 | Gibson et al. |
| 2011/0036346 A1* | 2/2011 | Cohen ............... A61M 15/0065 128/200.14 |
| 2011/0041861 A1 | 2/2011 | Sebastian et al. |
| 2011/0049226 A1 | 3/2011 | Moreau et al. |
| 2011/0094523 A1 | 4/2011 | Thorens et al. |
| 2011/0108023 A1 | 5/2011 | McKinney et al. |
| 2011/0155153 A1 | 6/2011 | Thorens et al. |
| 2011/0162667 A1 | 7/2011 | Burke et al. |
| 2011/0180433 A1 | 7/2011 | Rennecamp |
| 2011/0192397 A1 | 8/2011 | Saskar et al. |
| 2011/0226236 A1 | 9/2011 | Buchberger |
| 2011/0226266 A1 | 9/2011 | Tao |
| 2011/0232654 A1 | 9/2011 | Mass |
| 2011/0236002 A1 | 9/2011 | Oglesby et al. |
| 2011/0240047 A1 | 10/2011 | Adamic |
| 2011/0263947 A1* | 10/2011 | Utley .................. A61B 5/4845 600/300 |
| 2011/0265806 A1 | 11/2011 | Alarcon et al. |
| 2011/0268809 A1 | 11/2011 | Brinkley et al. |
| 2011/0277780 A1 | 11/2011 | Terry et al. |
| 2011/0278189 A1 | 11/2011 | Terry et al. |
| 2011/0315701 A1 | 12/2011 | Everson |
| 2012/0006342 A1 | 1/2012 | Rose et al. |
| 2012/0111347 A1 | 5/2012 | Hon |
| 2012/0199146 A1 | 8/2012 | Marangos |
| 2012/0204889 A1 | 8/2012 | Xiu |
| 2012/0227753 A1 | 9/2012 | Newton |
| 2012/0255567 A1 | 10/2012 | Rose et al. |
| 2012/0260927 A1 | 10/2012 | Liu |
| 2012/0267383 A1 | 10/2012 | Van Rooyen |
| 2012/0285475 A1 | 11/2012 | Liu |
| 2012/0291791 A1* | 11/2012 | Pradeep ................ A24F 47/008 131/273 |
| 2012/0318882 A1* | 12/2012 | Abehasera ........... A61M 11/041 239/1 |
| 2012/0325227 A1 | 12/2012 | Robinson et al. |
| 2013/0042865 A1 | 2/2013 | Monsees et al. |
| 2013/0068239 A1 | 3/2013 | Youn |
| 2013/0140200 A1 | 6/2013 | Scatterday |
| 2013/0152922 A1 | 6/2013 | Benassayag et al. |
| 2013/0174842 A1* | 7/2013 | Young ..................... A61L 9/032 128/203.14 |
| 2013/0186416 A1 | 7/2013 | Gao et al. |
| 2013/0199528 A1 | 8/2013 | Goodman et al. |
| 2013/0220315 A1* | 8/2013 | Conley ................ A24F 47/008 128/202.21 |
| 2013/0228191 A1 | 9/2013 | Newton |
| 2013/0247924 A1 | 9/2013 | Scatterday et al. |
| 2013/0248385 A1 | 9/2013 | Scatterday et al. |
| 2013/0255702 A1 | 10/2013 | Griffith, Jr. et al. |
| 2013/0276802 A1 | 10/2013 | Scatterday |
| 2013/0298905 A1 | 11/2013 | Levin et al. |
| 2013/0312742 A1 | 11/2013 | Monsees et al. |
| 2013/0319440 A1 | 12/2013 | Capuano |
| 2013/0333700 A1 | 12/2013 | Buchberger |
| 2013/0340775 A1 | 12/2013 | Juster et al. |
| 2014/0000638 A1 | 1/2014 | Sebastian et al. |
| 2014/0007891 A1 | 1/2014 | Liu |
| 2014/0014126 A1 | 1/2014 | Peleg et al. |
| 2014/0041655 A1 | 2/2014 | Barron et al. |
| 2014/0053856 A1 | 2/2014 | Liu |
| 2014/0053858 A1 | 2/2014 | Liu |
| 2014/0060552 A1 | 3/2014 | Cohen |
| 2014/0060556 A1 | 3/2014 | Liu |
| 2014/0096782 A1 | 4/2014 | Ampolini et al. |
| 2014/0109921 A1 | 4/2014 | Chen |
| 2014/0116455 A1 | 5/2014 | Youn |
| 2014/0123990 A1 | 5/2014 | Timmermans |
| 2014/0144429 A1 | 5/2014 | Wensley et al. |
| 2014/0150810 A1 | 6/2014 | Hon |
| 2014/0174459 A1 | 6/2014 | Burstyn |
| 2014/0190501 A1 | 7/2014 | Liu |
| 2014/0190503 A1 | 7/2014 | Li et al. |
| 2014/0196731 A1 | 7/2014 | Scatterday |
| 2014/0196735 A1 | 7/2014 | Liu |
| 2014/0216450 A1 | 8/2014 | Liu |
| 2014/0230835 A1 | 8/2014 | Saliman |
| 2014/0261474 A1 | 9/2014 | Gonda |
| 2014/0270727 A1 | 9/2014 | Ampolini et al. |
| 2014/0301721 A1 | 10/2014 | Ruscio et al. |
| 2014/0305450 A1 | 10/2014 | Xiang |
| 2014/0345631 A1 | 11/2014 | Bowen et al. |
| 2014/0345635 A1 | 11/2014 | Rabinowitz et al. |
| 2014/0355969 A1 | 12/2014 | Stern |
| 2014/0366898 A1 | 12/2014 | Monsees et al. |
| 2014/0378790 A1* | 12/2014 | Cohen .................... A61B 5/486 600/309 |
| 2015/0020823 A1 | 1/2015 | Lipowicz et al. |
| 2015/0020825 A1 | 1/2015 | Galloway et al. |
| 2015/0020831 A1 | 1/2015 | Weigensberg et al. |
| 2015/0027468 A1 | 1/2015 | Li et al. |
| 2015/0027472 A1 | 1/2015 | Amir |
| 2015/0034103 A1 | 2/2015 | Hon |
| 2015/0034104 A1 | 2/2015 | Zhou |
| 2015/0038567 A1 | 2/2015 | Herkenroth et al. |
| 2015/0040929 A1 | 2/2015 | Hon |
| 2015/0101625 A1 | 4/2015 | Newton et al. |
| 2015/0122252 A1 | 5/2015 | Frija |
| 2015/0122274 A1 | 5/2015 | Cohen et al. |
| 2015/0128965 A1 | 5/2015 | Lord |
| 2015/0128966 A1 | 5/2015 | Lord |
| 2015/0128967 A1 | 5/2015 | Robinson et al. |
| 2015/0128976 A1 | 5/2015 | Verleur et al. |
| 2015/0136153 A1 | 5/2015 | Lord |
| 2015/0136158 A1 | 5/2015 | Stevens et al. |
| 2015/0142387 A1 | 5/2015 | Alarcon et al. |
| 2015/0150308 A1 | 6/2015 | Monsees et al. |
| 2015/0157054 A1 | 6/2015 | Liu |
| 2015/0157056 A1 | 6/2015 | Bowen et al. |
| 2015/0164141 A1 | 6/2015 | Newton |
| 2015/0164144 A1 | 6/2015 | Liu |
| 2015/0164147 A1 | 6/2015 | Verleur et al. |
| 2015/0181928 A1 | 7/2015 | Liu |
| 2015/0189695 A1 | 7/2015 | Xiang |
| 2015/0196059 A1 | 7/2015 | Liu |
| 2015/0196060 A1 | 7/2015 | Wensley et al. |
| 2015/0208729 A1 | 7/2015 | Monsees et al. |
| 2015/0208731 A1 | 7/2015 | Malamud et al. |
| 2015/0216237 A1 | 8/2015 | Wensley et al. |
| 2015/0223521 A1 | 8/2015 | Menting et al. |
| 2015/0224268 A1 | 8/2015 | Henry et al. |
| 2015/0237917 A1 | 8/2015 | Lord |
| 2015/0237918 A1 | 8/2015 | Liu |
| 2015/0245654 A1 | 9/2015 | Memari et al. |
| 2015/0245660 A1 | 9/2015 | Lord |
| 2015/0257445 A1 | 9/2015 | Henry, Jr. et al. |
| 2015/0258289 A1 | 9/2015 | Henry, Jr. et al. |
| 2015/0272220 A1 | 10/2015 | Spinka et al. |
| 2015/0282525 A1 | 10/2015 | Plojoux et al. |

(56) References Cited

U.S. PATENT DOCUMENTS

| | | | |
|---|---|---|---|
| 2015/0282527 A1 | 10/2015 | Henry, Jr. |
| 2015/0305409 A1 | 10/2015 | Verleur et al. |
| 2015/0313275 A1 | 11/2015 | Anderson et al. |
| 2015/0313285 A1 | 11/2015 | Waller et al. |
| 2015/0320114 A1 | 11/2015 | Wu |
| 2015/0351456 A1 | 12/2015 | Johnson et al. |
| 2015/0366265 A1 | 12/2015 | Lansing |
| 2015/0366266 A1 | 12/2015 | Chen |
| 2016/0021931 A1 | 1/2016 | Hawes et al. |
| 2016/0021933 A1 | 1/2016 | Thorens et al. |
| 2016/0029698 A1 | 2/2016 | Xiang |
| 2016/0044967 A1 | 2/2016 | Bowen et al. |
| 2016/0044968 A1 | 2/2016 | Bowen et al. |
| 2016/0058071 A1 | 3/2016 | Hearn |
| 2016/0058072 A1 | 3/2016 | Liu |
| 2016/0081395 A1 | 3/2016 | Thorens et al. |
| 2016/0106154 A1 | 4/2016 | Lord |
| 2016/0106155 A1 | 4/2016 | Reevell |
| 2016/0120218 A1 | 5/2016 | Schennum et al. |
| 2016/0135503 A1 | 5/2016 | Liu |
| 2016/0143359 A1 | 5/2016 | Xiang |
| 2016/0143365 A1 | 5/2016 | Liu |
| 2016/0174611 A1 | 6/2016 | Monsees et al. |
| 2016/0227840 A1 | 8/2016 | Xiang |
| 2016/0242466 A1 | 8/2016 | Lord et al. |
| 2016/0249680 A1 | 9/2016 | Liu |
| 2016/0295924 A1 | 10/2016 | Liu |
| 2016/0302483 A1 | 10/2016 | Liu |
| 2016/0309784 A1 | 10/2016 | Silvestrini et al. |
| 2016/0324215 A1 | 11/2016 | Mironov et al. |
| 2016/0331033 A1 | 11/2016 | Hopp et al. |
| 2016/0331038 A1 | 11/2016 | Farine et al. |
| 2016/0331040 A1 | 11/2016 | Nakano et al. |
| 2016/0338410 A1 | 11/2016 | Batista et al. |
| 2016/0338411 A1 | 11/2016 | Liu |
| 2016/0345627 A1 | 12/2016 | Liu |
| 2016/0345630 A1 | 12/2016 | Mironov et al. |
| 2016/0368670 A1 | 12/2016 | Beardsall |
| 2016/0371464 A1 | 12/2016 | Bricker |
| 2016/0374390 A1 | 12/2016 | Liu |
| 2016/0374398 A1 | 12/2016 | Amir |

FOREIGN PATENT DOCUMENTS

| | | | |
|---|---|---|---|
| CN | 1122213 A | 5/1996 |
| CN | 101869356 A | 10/2010 |
| CN | 102754924 A | 10/2012 |
| DE | 4200639 A1 | 7/1992 |
| DE | 19854005 A1 | 5/2000 |
| DE | 19854012 A1 | 5/2000 |
| EP | 0532194 A1 | 3/1993 |
| EP | 0535695 A2 | 4/1993 |
| EP | 0283672 B1 | 9/1993 |
| EP | 1458388 A | 9/2004 |
| EP | 2325093 B1 | 6/2012 |
| EP | 2609821 A1 | 7/2013 |
| EP | 2152313 B1 | 9/2014 |
| EP | 3024343 A2 | 1/2015 |
| EP | 2856893 A1 | 4/2015 |
| EP | 2908675 A1 | 8/2015 |
| EP | 2319934 B1 | 9/2015 |
| EP | 2915443 A1 | 9/2015 |
| EP | 3062646 A1 | 9/2016 |
| EP | 3065581 A2 | 9/2016 |
| EP | 3068244 A1 | 9/2016 |
| ES | 2118034 A1 | 9/1998 |
| GB | 1025630 A | 4/1966 |
| GB | 1065678 A | 4/1967 |
| IE | S2005-0051 | 2/2005 |
| IE | S2005-0563 | 8/2005 |
| IE | S2005-0615 | 9/2005 |
| JP | 62-278975 | 12/1987 |
| JP | 64-37276 A | 2/1989 |
| JP | 02-145179 A | 6/1990 |
| JP | 03-049671 | 3/1991 |
| JP | 03-180166 | 8/1991 |
| JP | H06114105 A | 4/1994 |
| JP | 09-075058 | 3/1997 |
| JP | 10-501999 A | 2/1998 |
| JP | 11-178563 | 7/1999 |
| JP | 2000-203639 | 7/2000 |
| JP | 2000-236865 A | 9/2000 |
| JP | 2001-165437 A | 6/2001 |
| JP | 2001161819 A | 6/2001 |
| JP | 2005-034021 A | 2/2005 |
| JP | 2006-504430 A | 2/2006 |
| KR | 0193885 B1 | 6/1999 |
| WO | WO95/01137 A1 | 1/1995 |
| WO | WO97/12639 A1 | 4/1997 |
| WO | WO00/28842 A1 | 5/2000 |
| WO | WO03/056948 A1 | 7/2003 |
| WO | WO03/082031 A1 | 10/2003 |
| WO | WO03/094900 A1 | 11/2003 |
| WO | WO 03/103387 A2 | 12/2003 |
| WO | WO2004/064548 A1 | 8/2004 |
| WO | WO2004/080216 A1 | 9/2004 |
| WO | WO2005/020726 A1 | 3/2005 |
| WO | WO2006/015070 A1 | 2/2006 |
| WO | WO2007/026131 A1 | 3/2007 |
| WO | WO2007/078273 A1 | 7/2007 |
| WO | WO2008/077271 A1 | 7/2008 |
| WO | WO2010/023561 A1 | 3/2010 |
| WO | WO-2010118122 A1 | 10/2010 |
| WO | WO2011/033396 A2 | 3/2011 |
| WO | WO2011/117580 A2 | 9/2011 |
| WO | WO2012/021972 A1 | 2/2012 |
| WO | WO2012/027350 A2 | 3/2012 |
| WO | WO2012/085207 A1 | 6/2012 |
| WO | WO2012/120487 A2 | 9/2012 |
| WO | WO-2012174677 A1 | 12/2012 |
| WO | WO2013/044537 A1 | 4/2013 |
| WO | WO2013/050934 A1 | 4/2013 |
| WO | WO2013/083635 A1 | 6/2013 |
| WO | WO2013/089551 A1 | 6/2013 |
| WO | WO2013/098398 A2 | 7/2013 |
| WO | WO2013/142678 A1 | 9/2013 |
| WO | WO-2013156658 A1 | 10/2013 |
| WO | WO2014/040915 A1 | 3/2014 |
| WO | WO-2014067236 A1 | 5/2014 |
| WO | WO2014/093127 A2 | 6/2014 |
| WO | WO2014/101734 A1 | 7/2014 |
| WO | WO2014/118286 A2 | 8/2014 |
| WO | WO2014/139611 A1 | 9/2014 |
| WO | WO2014/140087 A1 | 9/2014 |
| WO | WO2014/150704 A2 | 9/2014 |
| WO | WO2014/159982 A1 | 10/2014 |
| WO | WO2014/187763 A1 | 11/2014 |
| WO | WO2014/187770 A2 | 11/2014 |
| WO | WO2014/205263 A1 | 12/2014 |
| WO | WO2015/006652 A1 | 1/2015 |
| WO | WO2015/009862 A2 | 1/2015 |
| WO | WO2015/028815 A1 | 3/2015 |
| WO | WO2015/040180 A2 | 3/2015 |
| WO | WO2015/058387 A1 | 4/2015 |
| WO | WO2015/063126 A1 | 5/2015 |
| WO | WO2015/082652 A1 | 6/2015 |
| WO | WO2015/084544 A1 | 6/2015 |
| WO | WO2015/089711 A1 | 6/2015 |
| WO | WO2015/101651 A1 | 7/2015 |
| WO | WO2015/109616 A1 | 7/2015 |
| WO | WO2015/124878 A1 | 8/2015 |
| WO | WO2015/148547 A1 | 10/2015 |
| WO | WO2015/149647 A1 | 10/2015 |
| WO | WO2015/168828 A1 | 11/2015 |
| WO | WO2015/169127 A1 | 11/2015 |
| WO | WO2015/175979 A1 | 11/2015 |
| WO | WO2015/179641 A1 | 11/2015 |
| WO | WO2015/193456 A1 | 12/2015 |
| WO | WO2016/012769 A1 | 1/2016 |

(56) References Cited

FOREIGN PATENT DOCUMENTS

| WO | WO2016/014652 A1 | 1/2016 |
|---|---|---|
| WO | WO2016/020675 A1 | 2/2016 |

OTHER PUBLICATIONS

Bullen et al.; Effect of an electronic nicotine delivery device (e cigarette) on desire to smoke and withdrawal, user preferences and nicotine delivery: randomised cross-over trial; Tobacco Control; 19(2); pp. 98-103; Apr. 2010.
Burch et al.; Effect of pH on nicotine absorption and side effects produced by aerosolized nicotine; Journal of Aerosol Medicine: Deposition, Clearance, and Effects in the Lung; 6(1); pp. 45-52; 1993.
Farsalinos et al.; Electronic cigarettes do not damage the heart; European Society of Cardiology; 4 pages; retrieved from the internet (http://www.escardio.org/The-ESC/Press-Office/Press-releases/Electronic-cigarettes-do-not-damage-the-heart); Aug. 25, 2012.
Flouris et al.; Acute impact of active and passive electronic cigarette smoking on serum cotinine and lung function; Inhal. Toxicol.; 25(2); pp. 91-101; Feb. 2013.
Food & Drug Administration; Warning letter to the Compounding Pharmacy; retrieved Oct. 10, 2014 from http://www.fda.gov/ICECI/EnfocementActions/WarningLetters/2002/ucm144843.htm; 3 pgs.; Apr. 9, 2002.
Goniewicz et al.; Nicotine levels in electronic cigarettes; Nicotine Tobacco Research; 15(1); pp. 158-166; Jan. 2013.
Harvest Vapor; American Blend Tobacco (product info.); retrieved from the internet (http://harvestvapor.com/); 2 pgs.; print/retrieval date: Oct. 10, 2014.
Inchem; Benzoic Acid; JECFA Evaluation Summary; retrieved Oct. 10, 2014 from http://www.inchem.org/documents/jecfa/feceval/jec_184.htm; 2 pgs..; May 28, 2005.
Inchem; Levulinic Acid; JECFA Evaluation Summary; retrieved Oct. 10, 2014 from http://www.inchem.org/documents/jecfa/feceval/jec_1266.htm; 1 pg.; Mar. 10, 2003.
Inchem; Pyruvic Acid; JECFA Evaluation Summary; retrieved Oct. 10, 2014 from http://www.inchem.org/documents/jecfa/feceval/jec_2072.htm; 1 pg.; Jan. 29, 2003.
Inchem; Sorbic Acid; JECFA Evaluation Summary; retrieved Oct. 10, 2014 from http://www.inchem.org/documents/jecfa/feceval/jec_2181.htm; 1 pg.; May 29, 2005.
Perfetti; Structural study of nicotine salts; Beitrage zur Tabakforschung International; Contributions to Tobacco Research; 12(2); pp. 43-54; Jun. 1983.
Seeman et al.; The form of nicotine in tobacco. Thermal transfer of nicotine and nicotine acid salts to nicotine in the gas phase; J Aric Food Chem.; 47(12); pp. 5133-5145; Dec. 1999.
Vansickel et al.; A clinical laboratory model for evaluating the acute effects of electronic cigarettes: Nicotine delivery profile and cardiovascular and subjective effects; Cancer Epidemiology Biomarkers Prevention; 19(8); pp. 1945-1953; (online) Jul. 20, 2010.
Vansickel et al.; Electronic cigarettes: effective nicotine delivery after acute administration; Nicotine & Tobacco Research; 15(1); pp. 267-270; Jan. 2013.
Zhang et al.; In vitro particle size distributions in electronic and conventional cigarette aerosols suggest comparable deposition patterns; Nicotine Tobacco Research; 15(2); pp. 501-508; Feb. 2013.
Grotenhermen et al.; Developing science-based per se limits for driving under the influence of cannabis (DUIC): findings and recommendations by an expert panel; retrieved Feb. 9, 2017 from (http://www.canorml.org/healthfacts/DUICreport.2005.pdf); 49 pages; Sep. 2005.
Monsees et al.; U.S. Appl. No. 15/368,539 entitled "Low temperature electronic vaporization device and methods," filed Dec. 2, 2016.
Bowen et al.; U.S. Appl. No. 15/309,554 entitled "Systems and methods for aerosolizing a smokeable material," filed Nov. 8, 2016.

Monsees et al.; U.S. Appl. No. 15/379,898 entitled "Vaporization device systems and methods," filed Dec. 15, 2016.
Hatton et al.; U.S. Appl. No. 15/396,584 entitled "Leak-resistant vaporizer cartridges for use with cannabinoids," filed Dec. 31, 2016.
Capponnetto et al.; Successful smoking cessation with cigarettes in smokers with a documented history of recurring relapses: a case series; Journal of Medical Case Reports; 5(1); 6 pages; (year of pub. sufficiently earlier than effective US filed and any foreign priority date); 2011.
Hurt et al.; Treating tobacco dependence in a medical setting; CA: A Cancer Journal for Clinicians; 59(5); pp. 314-326; Sep. 2009.
Monsees et al.; U.S. Appl. No. 15/257,748 entitled "Cartridge for use with a vaporizer device," filed Sep. 6, 2016.
Monsees et al.; U.S. Appl. No. 15/257,760 entitled "Vaporizer apparatus," filed Sep. 6, 2016.
Monsees et al.; U.S. Appl. No. 15/257,768 entitled "Vaporizer apparatus," filed Sep. 6, 2016.
E-Cigarette Forum; pg-gv-peg (discussion/posting); retrieved from the internet: https://e-cigarette-forum.com/forum/threads/pg-vg-peg.177551; 7 pgs.; Apr. 8, 2011.
Monsees et al.; U.S. Appl. No. 15/165,954 entitled "Devices for vaporization of a substance," filed May 26, 2016.
Monsees et al.; U.S. Appl. No. 15/166,001 entitled "Electronic vaporization device," filed May 26, 2016.
Monsees et al.; U.S. Appl. No. 15/165,972 entitled "Portable devices for generating an inhalable vapor," filed May 26, 2016.
Bowen et al.; U.S. Appl. No. 15/101,303 entitled "Nicotine liquid formulations for aerosol devices and methods thereof," filed Jun. 2, 2016.
Monsees et al.; U.S. Appl. No. 15/261,823 entitled "Low temperature electronic vaporization device and methods," filed Sep. 9, 2016.
Baker et al.; The pyrolysis of tobacco ingredients; J. Anal. Appl. Pyrolysis; 71(1); pp. 223-311; Mar. 2004.
Bombick et al.; Chemcal and biological studies of a new cigarette that primarily heats tobacco; Part 3: In vitro toxicity of whole smoke; Food and Chemical Toxicology; 36(3); pp. 191-197; Mar. 1998.
Bombick et al.; Chemical and biological studies of a new cigarette that primarily heats tobacco; Part 2: In vitro toxicology of mainstream smoke condesnsate; Food and Chemical Toxicology; 36(3); pp. 183-190; Mar. 1998.
Borgerding et al.; Chemcal and biological studies of a new cigarette that primarily heats tobacco; Part 1: Chemical composition of mainstream smoke; Food and Chemical Toxicology; 36(3); pp. 169-182; Mar. 1998.
ECF; Any interest in determining nicotine—by DVAP; (https://www.e-cigarette-forum.com/forum/threads/any-interest-in-determining-nicotine-by-dvap.35922/); blog posts dated: 2009; 8 pgs.; print/retrieval date: Jul. 31, 2014.
Ingebrethsen et al.; Electronic cigarette aerosol particle size distribution measurements; Inhalation Toxicology; 24(14); pp. 976-984; Dec. 2012.
Kuo et al.; Appendix D: Particle size—U.S. sieve size and tyler screen mesh equivalents; Applications of Turbulent and Multiphase Combustion; John Wiley & Sons, Inc.; pp. 541-543; May 1, 2012.
McCann et al.; Detection of carcinogens as mutagens in the *Salmonella*/microsome test: Assay of 300 chemicals: Discussion; Proc. Nat. Acad. Sci.; 73(3); pp. 950-954; Mar. 1976.
Mirriam-Webster Online Dictionary; Lighter; retrieved Jan. 4, 2013 from the internet: (http://www.merriam-webster.com/dictionary/lighter?show=0&t=1357320593); 2 pgs.; print date: Jan. 4, 2013.
Nicoli et al.; Mammalian tumor xenografts induce neovascularization in Zebrafish embryos; Cancer Research; 67(7); pp. 2927-2931; Apr. 1, 2007.
Torikai et al.; Effects of temperature, atmosphere and pH on the generation of smoke compounds duriung tobacco pyrolysis; Food and Chemical Toxicology; 42(9); pp. 1409-1417; Sep. 2004.
Ward; Green leaf threshing and redrying tobacco; Section 10B; in Tobacco Production, Chemistry and Technology; Davis and Nielsen (Eds.); Blackwell Science Ltd.; pp. 330-333; Jul. 15, 1999.
Wells; Glycerin as a constituent of cosmetics and toilet preparations; Journal of the Society of Cosmetic Chemists; 9(1); pp. 19-25; Jan. 1958.

(56) References Cited

OTHER PUBLICATIONS

YouTube; Firefly Vaporizor Review w/ Usage Tips by The Vape Critic; retrieved from the internet (http://www.youtube.com/watch?v=1J38N0AV7wl); 1 pg.; published Dec. 10, 2013; download/print date: Feb. 18, 2015.
Monsees, J.; U.S. Appl. No. 12/115,400 entitled "Method and System for Vaporization of a Substance", dated May 5, 2008.
Bowen et al.; U.S. Appl. No. 14/960,259 entitled "Calibrated Dose Control", dated Dec. 4, 2015.
Andrew Gregory, "E-Cigarettes to Go on Prescription Under Move to Class Them as Medicines", Mirror, Jun. 12, 2013, confirmed by archive.org to have existed as of Jun. 12, 2013.
SRNT Subcommittee on Biochemical Verification, "Biochemical Verification of Tobacco Use and Cessation", Nicotine and Tobacco Research, 2002, pp. 149-159.
Richard D. Hurt, Jon O. Ebbert, J. Taylor Hays, and David D. McFadden, "Treating Tobacco Dependence in a Medical Setting", CA: A Cancer Journal for Clinicians, Aug. 25, 2009, pp. 314-26.
Pasquale Caponnetto, Riccardo Polosa, Cristina Russo, Carmelo Leotta and David Campagna, "Successful smoking cessation with electronic cigarettes in smokers with a documented history of recurring relapses: a case series"Journal of Medical Case Reports, 2011.
Polosa, Riccardo, et al., "Effect of an electronic nicotine delivery device (e-Cigarette) on smoking reduction and cessation: a prospective 6-month pilot study." BMC public health 11.1 (2011): 786 (12 pages).
SRNT Subcommittee on Biochemical Verification, "Biochemical verification of tobacco use and cessation," Nicotine & Tobacco Research 4, pp. 149-159, 2002.
Andrew Gregory, "E-Cigarettes to Go on Prescription Under Move to Class Them as Medicines", Mirror, Jun. 12, 2013, confirmed by archive.org to have existed as of Jun. 12, 2013 (8 pages).

* cited by examiner

Prescriber / Dispenser Authorization and Verification

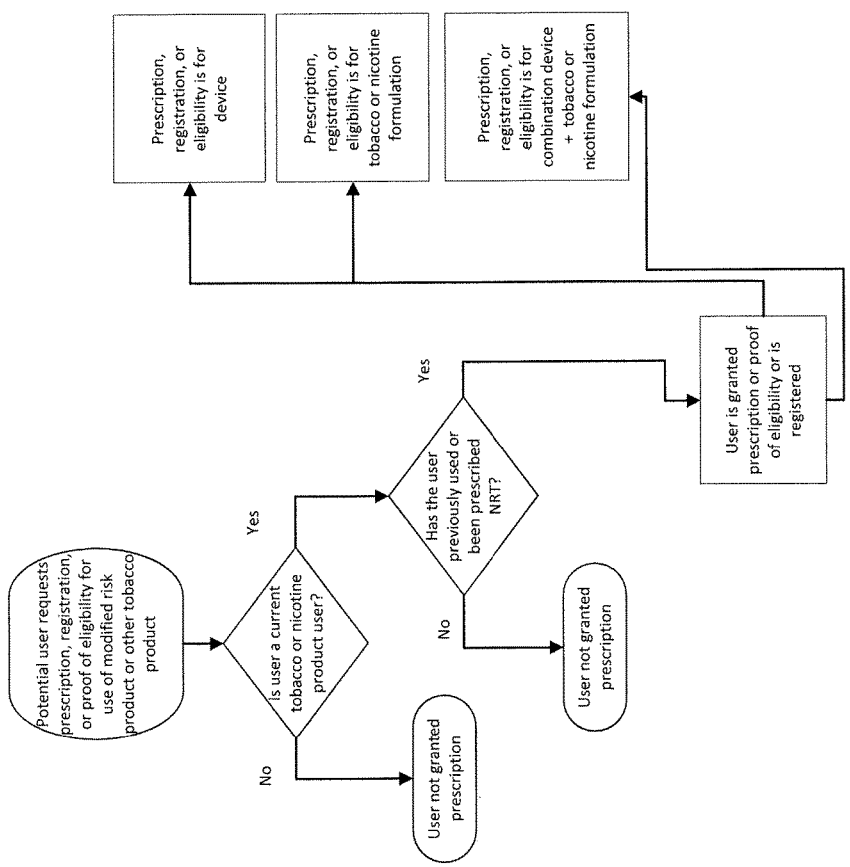

| Biochemical Markers | Cut-off Value |
|---|---|
| Carbon Monoxide | |
| ECO (ppm) | 8 |
| COHb (%) | 1.6 |
| Nicotine (ng/ml) | |
| Plasma | 2.3 |
| Saliva | 21.8 |
| Urine | 58.6 |
| Cotinine (ng/ml) | |
| Plasma | 13.7 |
| Saliva | 14.2 |
| Urine | 49.7 |
| Thiocyanate | |
| Plasma ($\mu mol/l$) | 78.0 |
| Saliva ($mmol/l$) | 1.64 |
| Urine ($\mu mol/l$) | 118.0 |

Fig. 3E

User Verification for Modified Risk Product Mitigation and Tracking

Program compliance verification

METHODS AND DEVICES FOR DELIVERING AND MONITORING OF TOBACCO, NICOTINE, OR OTHER SUBSTANCES

CROSS-REFERENCE TO RELATED APPLICATIONS

This application is a continuation-in-part of U.S. patent application Ser. No. 14/012,952, titled "METHODS AND DEVICES FOR DELIVERY AND MONITORING OF TOBACCO, NICOTINE, OR OTHER SUBSTANCES," filed Aug. 28, 2013, now U.S. Patent Application Publication No. 2014-0060552, which claims the benefit of U.S. Provisional Patent Application No. 61/694,046, titled "METHODS AND DEVICES FOR DELIVERY AND MONITORING OF TOBACCO, NICOTINE, OR OTHER SUBSTANCES," filed Aug. 28, 2012, each of which is herein incorporated by reference in its entirety.

BACKGROUND OF THE INVENTION

The use of tobacco products and the harmful side effects of smoking tobacco and nicotine consumption continue to gain increasing attention worldwide. As more regulations come into effect regarding smoking in the work place or in public, interest in developing alternative methods of protecting public health and providing cessation products and methods is growing significantly. As with most new therapies or drugs, the federal government has issued regulations intended to protect the public, with enforcement authority granted to the U.S. Food and Drug Administration (FDA).

SUMMARY OF THE INVENTION

It is generally understood that the mission of the US Food and Drug Administration (FDA) is to advance the public health by helping to speed the innovations that make medicines and most foods more effective, safer, and more affordable; and help the public get accurate, science-based information they need to use those medicines and foods to improve their health.

In June, 2009, The Family Smoking Prevention and Tobacco Control Act was signed into law, creating "The Center for Tobacco Products", a tobacco control center within the FDA, having the authority to regulate tobacco industry in the U.S., by regulating the content, commercial marketing, sale and distribution of tobacco products within the United States. The law also requires tobacco companies and importers to reveal all product ingredients and seek FDA approval for any new tobacco products.

Under its new-found, expanded authority, the FDA now has the ability to control the commercial sale and distribution of traditional tobacco products, including cigarettes, pipe tobacco, and cigars, as well as new tobacco and nicotine related products, including; electronic nicotine vaporizers, (e.g. the electronic cigarette); and products with potentially modified safety risk relative to cigarettes. These products have new regulatory pathways associated with them, including those proscribed under Section 911 (modified risk tobacco products.)

When considering whether to allow the marketing of modified risk products or other novel or new but substantially equivalent tobacco products, FDA must consider the benefit to health of individuals and the population as a whole, including: "the increased or decreased likelihood that existing users of tobacco products who would otherwise stop using such products will switch to the tobacco product that is the subject of the application; the increased or decreased likelihood that persons who do not use tobacco products will start using the tobacco product that is the subject of the application; and the risks and benefits to persons from the use of the tobacco product that is the subject of the application as compared to the use of products for smoking cessation approved under chapter V to treat nicotine dependence."

One potential approach for FDA to address the benefits to health of individuals and the population could be to require Risk Evaluation and Mitigation Strategies (REMS) be put in place for modified risk products or other tobacco products as a prerequisite for marketing approval.

There are essentially three components to a REMS program: 1. A medication guide or patient insert; 2. A communication plan for healthcare providers; and 3. Elements to assure safe use, (ELASU). A drug's REMS program may not require the provision of all three components, as the specific components a REMS program employs will vary based on the severity of the risks, the population likely to be exposed, and other factors. In fact, the most common REMS only require the provision of a medication guide.

While REMS components are not uniform, some currently do, or in the future, may contain new provisions and requirements for physicians and other certified health care providers. For REMS requiring ETASU, clinicians may be required to: Obtain and dispense drugs through specific distribution channels; Possess specific training, education, experience, or certification(s) in order to prescribe these drugs; Enroll patients in registry programs; and, Issue mandatory, time-sensitive reports of patient responses to treatment.

It is possible that one's ability to prescribe and dispense certain medications, even some that have been on the market for years, could be contingent upon compliance with these REMS provisions.

Applicant has developed novel methods and devices for the delivery and monitoring of tobacco, nicotine and other substances that will meet or exceed any potential federal regulation in this field.

Provided herein is a method of protecting public health comprising: increasing the likelihood that a first subject or a second subject will stop using a tobacco product by providing a modified risk product or other tobacco product for administration to the first subject addicted to the tobacco product wherein the first subject has previously failed nicotine replacement therapy.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided, or a subject's eligibility is verified by a physician, a nurse, a pharmacist, an accredited healthcare provider, or an employee of a convenience or retail store.

In some embodiments, the product is prescribed, provided, or a subject's eligibility is verified by an internet or wireless based application, service or business, or by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine, nicotine by-product levels, CO levels, or other biomarker levels are above or consistent with levels expected for a tobacco or nicotine user.

In some embodiments, the subject compliance verification comprises collecting and sending samples, taken before (and/or in some variations, after) being provided a modified risk product, for analysis to an accredited testing facility, and measuring the difference between said samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising: increasing the likelihood that a first subject or a second subject will stop using a tobacco product by providing a modified risk product or other tobacco product for administration to the first subject addicted to the tobacco product only after at least one failed attempt by the first subject to quit using such tobacco product. In general, modified risk products or other tobacco products may include tobacco and/or nicotine delivery devices including, for example: an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed at least one attempt to quit using said tobacco product comprises, abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided, administered, or subject eligibility verified by a physician, a nurse, a pharmacist, or an accredited healthcare provider, or an employee of a convenience or retail store.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising increasing the likelihood that a first subject or a second subject will stop using a tobacco product by providing a modified risk product or other tobacco product for administration to the first subject addicted to the tobacco product only after the modified risk product or other tobacco product is prescribed to the first subject.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the product is prescribed by a physician, a nurse, a pharmacist, or an accredited healthcare provider.

In some embodiments, the risk evaluation and mitigation strategy incorporates a means of subject compliance verification.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product wherein the first subject has previously failed nicotine replacement therapy.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed attempt to quit using said tobacco product comprises, abstinence, nicotine gum, nicotine oral spray, nicotine inhaler, nicotine nasal spray, nicotine lozenge, nicotine dermal patch, Bupropion, Chantix, or comparable oral nicotine replacement product.

In some embodiments, the product is prescribed, provided or subject eligibility verified by a physician, a nurse, a pharmacist, or an accredited healthcare provider.

In some embodiments, the product is provided or subject eligibility verified by an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine, nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product only after at least one failed attempt by the first subject to quit using such tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the previously failed attempt to quit using said tobacco product comprises, abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided or subject eligibility verified by a physician, a nurse, a pharmacist, or an accredited healthcare provider.

In some embodiments, the product is provided or subject eligibility verified by or an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of protecting public health comprising decreasing the likelihood that a second subject not using a tobacco product will start using the tobacco product or an alternative tobacco product, by providing a modified risk product or other tobacco product for administration to the first subject addicted to the tobacco product, only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by and subject eligibility verified by a physician, a nurse, a pharmacist, or an accredited healthcare provider.

In some embodiments, the product is provided or subject eligibility verified by or an employee of a convenience or retail store.

In some embodiments, the product is provided, or subject eligibility verified by an internet based application, service or business.

In some embodiments, the product is provided or subject eligibility verified by a call center or phone based application service or business.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

Provided herein is a method of treating a first subject addicted to a tobacco product, the method comprising administering to the first subject who has previously failed nicotine replacement therapy, a modified risk product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, CO levels, or other biomarker levels in blood samples, in expelled breath samples, in saliva samples, in hair samples, and in urine samples to verify that the subject's nicotine or nicotine by-product levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by or an employee of a convenience or retail store.

Provided herein is a method of treating a first subject addicted to a tobacco product, the method comprising administering to the first subject a modified risk product or other tobacco product only after at least one failed attempt by the first subject to quit using such tobacco product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method of treating a first subject addicted to a tobacco product, the method comprising administering a modified risk product or other tobacco product to the first subject only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the modified risk product or other tobacco product is prescribed and administered by a physician, a nurse, a pharmacist, or an accredited healthcare provider.

In some embodiments, the product is administered by an accredited employee of a convenience or retail store, or an employee of an accredited convenience or retail store.

In some embodiments, the product is administered by an internet or wireless based application, service or business.

In some embodiments, the product is administered by a call center or phone based application service or business.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood, expelled breath, saliva, hair, and/or urine.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method for increasing the likelihood that the first subject or a second subject will stop using the tobacco product.

Provided herein is a method for decreasing the likelihood that a second subject not using the tobacco product will start using the tobacco product.

Provided herein is a method for verifying the at least one prior failed attempt to stop using tobacco products prior to the modified risk product or other tobacco product being provided to a first subject.

In some embodiments, the verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user after verification that the subject had previously attempted to stop using tobacco products.

In some embodiments, the previously failed attempt may have comprised using abstinence, nicotine gum, nicotine oral spray, nicotine inhaler, nicotine nasal spray, nicotine lozenge, nicotine dermal patch, Bupropion®, Chantix®, or comparable oral nicotine replacement product.

Provided herein is a method for verifying that a first subject meets at least one eligibility requirement for use of a modified tobacco risk product.

Provided herein is a method for verifying a subject's eligibility requirement comprising: possession of an eligibility card, meeting qualifications for the eligibility card, possessing a valid verification code, possessing a physician-provided eligibility record, possessing a pharmacist-provided eligibility record, and passing a pharmacist-provided eligibility evaluation.

In some embodiments of a method having an eligibility requirement, the identity verification step comprises at least one of:

evidence of meeting a minimum age requirement, evidence of a previously failed nicotine replacement therapy, and evidence of a at least one failed attempt by the patient to quit using such tobacco product, electronic or telephonic verification of a unique subject eligibility card or code identifier, software verification of a unique subject eligibility card or code identifier, electronic fingerprint verification of an eligible subject, an activation code, or an electronic dongle, electronic security key fob, or equivalent.

Provided herein is a method for verifying a subject's eligibility requirement wherein the verifying step is performed by a physician, a nurse, a pharmacist, an accredited healthcare provider an accredited employee of a convenience or retail store, or an employee of an accredited convenience or retail store.

Provided herein is a method for providing a prescription for a modified risk product, wherein said prescription is provided by a qualified healthcare provider.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

Provided herein is a method of verifying eligibility of a first subject addicted to a tobacco product, to be provided with a modified risk product, the method comprising, measuring nicotine levels, nicotine levels, CO levels, or other biomarker levels present in the system of a first subject prior to administration of said modified risk product or other tobacco product and confirming that said nicotine levels, nicotine levels, CO levels, or other biomarker levels are above or consistent with those of a tobacco or nicotine product user.

In some embodiments the method of verifying eligibility comprises; measuring nicotine levels, nicotine levels, CO levels, or other biomarker levels in blood samples, expelled breath samples, saliva samples, hair samples, and urine samples.

Provided herein is a method of monitoring compliance of a first subject addicted to a tobacco product and participating in a REMS program comprising a modified risk product, the method comprising, measuring nicotine levels, nicotine levels, CO levels, or other biomarker levels of a first subject prior to administration of said modified risk product or other tobacco product and measurement of nicotine levels, nicotine levels, CO levels, or other biomarker levels after administration of said modified risk product, and comparing said prior nicotine prior levels, nicotine levels, CO levels, or other biomarker levels to anticipated nicotine levels, nicotine levels, CO levels, or other biomarker levels after administration of said modified risk product.

In some embodiments, a method of monitoring comprises; using an electronic signature to track the pattern of use of a vaporizer, electronic cigarette, or other modified risk product or other tobacco product wherein said product transmits a record of use over a given period of time.

In some embodiments, a record of use comprises levels of nicotine consumed, times, and dates it was consumed.

In some embodiments, the record of use is stored to a data storage device and later downloaded for use by a qualified healthcare provider or REMS monitor or administrator.

In some embodiments, the record of use is transmitted wirelessly to a data storage device and later downloaded for use by a qualified healthcare provider or REMS monitor or administrator.

In some embodiments, the record of use is stored within the device, and later downloaded for use by a qualified healthcare provider or REMS monitor.

In some embodiments, the record of use may be wirelessly transmitted from a data storage device or a component of the modified risk product or other tobacco product to a remote location for use by a qualified healthcare provider or REMS monitor or administrator.

Provided herein is a method of monitoring the use of a modified risk product or other tobacco product by a first subject addicted to a tobacco product, the method comprising, requiring an identification recognition system be activated before use of a modified risk product or other tobacco product can occur.

In some embodiments, the identification recognition system comprises a fingerprint scanner, a lip print scanner, face recognition, a retinal scan, a combination code, an activation code, security key fob, or dongle.

In some embodiments, the identification recognition system comprises an electronic application for a smartphone, laptop, desktop, or tablet computing device, capable of communicating with the modified risk product or other tobacco product by a wireless communication system.

In some embodiments, the identification recognition system must be within a fixed distance of the modified risk product or other tobacco product for product to continue to work.

In some embodiments, the identification recognition system must be within about 5 to 20 feet of the modified risk product.

In some embodiments, the identification recognition system must be within 10 feet of the modified risk product.

In some embodiments, the identification recognition system must be within 5 feet of the modified risk product.

Provided herein is a method of protecting the public health comprising increasing the likelihood that a first subject will stop using a tobacco product by providing a modified risk product or other tobacco product for administration to the first subject addicted to the tobacco product wherein the modified risk product or other tobacco product provides a faster onset of nicotine delivery, or a higher peak level of nicotine delivery.

Provided herein is a method of risk mitigation wherein the potential risk of misuse or abuse of a modified risk product or other tobacco product is ranked or stratified in comparison to other tobacco products.

In some embodiments, the relative potential risk of the modified risk product or other tobacco product is determined by comparing the pharmacokinetic profile of the modified risk product or other tobacco product to nicotine.

In some embodiments the pharmacokinetic profile of the modified risk product or other tobacco product is determined by the maximum plasma concentration (Cmax) of nicotine, compared to a cigarette.

In some embodiments the pharmacokinetic profile of the modified risk product or other tobacco product is determined by the time after administration of the product for nicotine to reach maximum plasma concentration (Tmax), compared to a cigarette.

In some embodiments the pharmacokinetic profile of the modified risk product or other tobacco product is determined by the rate-of-increase of nicotine delivery or concentration in the plasma of a subject compared to a cigarette.

In some embodiments, the relative potential risk of the modified risk product or other tobacco product is determined by comparing the nicotine concentration of the modified risk product or other tobacco product other nicotine products in the market.

In some embodiments, the relative potential risk of the modified risk product or other tobacco product is ranked by ease of access associated with the prescriber/administrator.

In some embodiments, the relative potential risk of the modified risk product or other tobacco product is ranked by ease of access through various distribution channels.

In some embodiments the modified risk product or other tobacco product comprises vaporizing tobacco leaves above their pyrolytic temperature.

In some embodiments the modified risk product or other tobacco product comprises heating tobacco leaves below their pyrolytic temperature.

In some embodiments the modified risk product or other tobacco product comprises vaporization of a nicotine salt.

In some embodiments the modified risk product or other tobacco product comprises heating of a nicotine salt below its pyrolytic temperature.

Provided herein is a method of protecting the public health wherein the provider of a modified risk product or other tobacco product is subject to a compliance verification system.

In some embodiments, the provider verification is performed by an independent auditor.

Provided herein is a system for verification of subject eligibility, tracking, and reporting use of a modified risk product or other tobacco product comprising: an electronic cigarette, an electronic pipe, an electronic cigar, an electronic water pipe, or an electronic vaporizer, comprising a battery, an atomizer, electronic circuitry, a memory storage device for tracking components of usage activity, a means of memory transfer, and a charging circuit, a charger base station comprising a memory storage device, a means for receiving data from said modified risk product or other tobacco product memory storage device and transmitting said data to a third party, activation software for recognition of a specific device, keyed to said charger base, capable of interfacing with an external device, wherein said external device comprises; a smart phone, computer, electronic fob, electronic dongle, and a wireless communication device, e.g.: Bluetooth device.

In some embodiments, the system is used in combination with a risk evaluation and mitigation strategy.

In some embodiments, the system comprises activation means, for recognition and verification of a subject to establish user eligibility prior to use.

In some embodiments, the system is used to verify subject compliance for use of a modified risk product.

In some embodiments the system comprises a means for validating overall success of the risk mitigation product when used with the risk evaluation and mitigation strategies.

In general, in one embodiment, a method of providing a verification of eligibility for use or purchase of a tobacco product includes: (1) administering a diagnostic test to a subject; (2) determining whether the subject has previously used a tobacco product based upon results of the diagnostic test; and (3) providing a verification of eligibility for use or purchase of a tobacco product if results for the diagnostic test indicate that the subject has previously used a tobacco product.

This and other embodiments can include one or more of the following features. The step of determining can include determining from a saliva, blood, or urine test for nicotine, cotinine, or nicotine by-products. The step of determining can include determining from a carbon monoxide breath analysis. The step of determining can include determining if the subject's breath has a reading of greater than 5 ppm CO which can indicate that the subject previously used a tobacco product. The step of determining can include determining if the subject's breath has a reading of greater than 10 ppm which can indicate that the subject previously used a tobacco product. The step of determining can include determining whether the subject has consumed a tobacco product within the last 24 hours. The step of determining can include determining whether the subject has consumed a tobacco product on a regular basis, and the step of providing a verification of eligibility can include providing the verification for eligibility only if the subjected has consumed the tobacco product on a regular basis. The step of determining can include determining whether the subject has previously consumed combustible tobacco. The step of determining can include determining whether the subject has previously consumed tobacco from an electronic cigarette, an electronic pipe, an electronic cigar, an electronic water pipe, or an electronic vaporizer. Providing the subject with the verification of eligibility can include providing at least one of: a prescription from a physician or accredited healthcare provider, an eligibility card or code identifier, an activation code, an electronic dongle, a listing in a database, or an electronic security key fob. Determining and providing steps can be provided by a physician, nurse, pharmacists, accredited healthcare provider, an employee of a convenience or retail store, an internet or wireless based application, a service or business, a call center or phone based application, or a service or business.

In general, in one embodiment, a method of providing a verification of eligibility for use or purchase of a tobacco product includes: (1) sampling a subject's breath; (2) determining, from the subject's breath, whether the subject has previously used a tobacco product based upon results of the diagnostic test; and (3) providing the subject with a verification of eligibility for use or purchase of a tobacco product if the subject has previously used a tobacco product based on the determination from the subject's breath.

This and other embodiments can include one or more of the following features. The step of determining can include determining from a carbon monoxide breath analysis. The step of determining can include determining if the subject's breath has a reading of greater than 5 ppm CO which can indicate that the subject previously used a tobacco product. The step of determining can include determining if the subject's breath has a reading of greater than 10 ppm which can indicate that the subject previously used a tobacco product. The step of determining can include determining that the subject has consumed a tobacco product within the last 24 hours. The step of determining can include determining whether the subject has consumed a tobacco product on a regular basis, and wherein the step of providing a verification of eligibility can include providing the verification for eligibility only if the subjected has consumed tobacco products on a regular basis. The step of determining can include determining whether the subject has previously consumed combustible tobacco. The step of determining can include determining whether the subject has previously consumed tobacco from an electronic cigarette, an electronic pipe, an electronic cigar, an electronic water pipe, or an electronic vaporizer, or other non-combustion tobacco product. Providing the subject with the verification of eligibility can include providing at least one of: a prescription from a physician or accredited healthcare provider, an eligibility card or code identifier, an activation code, an electronic dongle, a listing in a database, or an electronic security key fob. Determining and providing steps can be provided by a physician, nurse, pharmacists, accredited healthcare provider, an employee of a convenience or retail store, an internet or wireless based application, a service or business, a call center or phone based application, or a service or business.

In general, in one embodiment, a method of providing a tobacco product includes: (1) determining whether a subject has previously used a tobacco product based on a diagnostic assay performed on the subject; and (2) providing a tobacco product to the subject if the diagnostic assay indicates that the subject has previously used a tobacco product.

This and other embodiments can include one or more of the following features. The step of determining can include determining at the point of sale. The step of determining can include performing the diagnostic assay using a sensor on the tobacco product. The step of determining can include performing the diagnostic assay. The step of determining can include looking up the results of the diagnostic assay in a database using a unique identifier of the subject. The tobacco product can include an electronic cigarette, an electronic pipe, an electronic cigar, an electronic water pipe, or an electronic vaporizer. The step of determining can include determining whether the subject has previously used a tobacco product based on a diagnostic test which can include a carbon monoxide breath analysis. The step of determining can include determining whether the subject has previously used a tobacco product based on a diagnostic test which can include a carbon monoxide breath analysis, wherein a reading of greater than 5 ppm CO in a breath sample can indicate that the subject has previously used a tobacco product. The step of determining can include determining whether the subject has previously used a tobacco product based on a diagnostic test which can include a saliva, blood, or urine test for nicotine, cotinine, or nicotine by-products.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a possible configuration of a REMS component program for the authorization and dispensation of prescriptions for a Modified risk product or other tobacco product or other tobacco product when a subject has previously used a nicotine replacement therapy;

FIG. 3E is a table showing exemplary cut-off values for various biomarkers such that a subject's measured level of the biomarker above the cut-off value indicates eligibility for a modified risk or other tobacco product;

DETAILED DESCRIPTION OF THE INVENTION

Figure 1A:
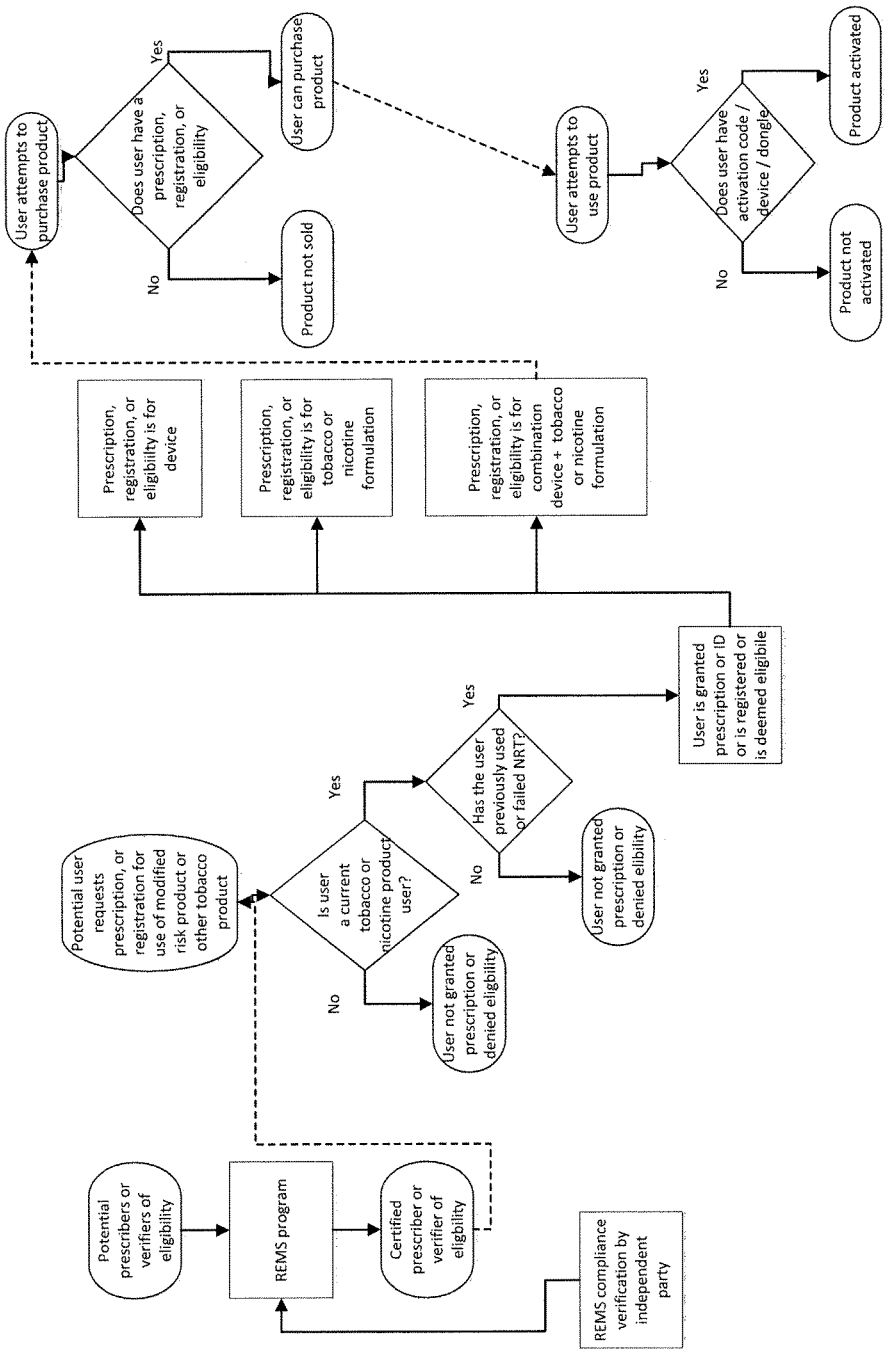
FIG. 1A illustrates a possible configuration of an overall Risk Evaluation and Mitigation Strategy (REMS) where a subject has previously used a nicotine replacement therapy.

Provided herein are methods of protecting the public health by increasing the likelihood that a subject addicted to a tobacco product will stop using a tobacco product wherein the subject has previously failed to stop using a tobacco product by other means.

It should be understood that at a minimum, terms used throughout this specification have the following meanings:

Definitions

Abstinence: Abstinence has diverse forms and several potential definitions. Commonly it refers to a temporary or partial refrain from food, alcohol, sexual activity, or drugs, such as nicotine in tobacco products. Alternately, it could be used to describe total abstinence where something is completely removed from one's lifestyle for a period of time. As it applies herein, abstinence is generally intended to have the more common meaning of temporary or partial, self-enforced, restraint from indulgence. However, the term may also imply long-term restraint, wherein a subject has maintained a sustained abstinence; i.e.: several years, without necessarily having quit using said products entirely.

Administer/Administration: Is intended to mean that a product or service has been provided to a subject. Such service may include performing a test, delivering a prescription, or carrying out/providing a verification process.

Fail/Failed/Failure: is intended to mean that a subject has not succeeded with a previous therapy and returned to previous levels (or greater levels) of tobacco product use. It is commonly understood in therapy programs that early "failure" is a normal part of trying to stop, and more than one attempt at stopping smoking prior to longer-term success is common. Alternatively it could mean inability to refrain from total or sustained abstinence.

Fail/Failed/Failure: May also mean that a subject continues to use a NRT product longer than indicated by the prescribing method or suggested use, with or without additional use of a tobacco product in addition to the NRT product. For example; a subject may continue using a nicotine patch while continuing to smoke cigarettes, beyond the intended "weaning off" period.

Initiate: Is intended to mean that a subject has at some point begun using any tobacco cessation therapy or Nicotine Replacement Therapy (NRT) product.

Modified Risk Product: Is intended to mean a tobacco product that is sold, distributed, or marketed under regulatory authority, with a claim to reduce harm or the risk of tobacco related diseases, or a tobacco product that is shown to substantially reduce the overall exposure to harmful substances.

Modified Risk Product: May also mean a tobacco or nicotine delivery device or product that is sold, distributed, or marketed under regulatory authority comprising a non-combustion-based, or vaporization-based nicotine delivery mechanism with a lower risk factor for one or more tobacco related diseases or exposure to one or more harmful substances, which may be substituted for any other oral, combustion, or vaporization-based nicotine delivery product having a higher risk factor for one or more tobacco related diseases or exposure to one or more harmful substances.

Prescribe/Prescription: Is intended to mean that a product has been authorized for distribution to a subject by order of an accredited healthcare provider (a physician); i.e.: by prescription (Rx).

Prescribe: May also mean a commonly available over-the-counter product that has been recommended by an accredited healthcare provider (a physician, a nurse, a pharmacist); i.e.: by suggestion the use an OTC product, not requiring a Rx, but still requiring verification of a type to meet local, state, or federal regulation by an accredited individual, at the point of distribution. Alternately a person may self-prescribe an available OTC product.

Quit: is intended to mean that a subject has completely stopped using a (tobacco) product; i.e.: total (i.e.: smoking) cessation.

Tobacco product: Is generally intended to mean any product produced from any genus of *Nicotiana* plants or nightshade family of plants, or a by-product derived therefrom, comprising nicotine, nicotine salts, or nicotine derivatives, which may produce by-products that can be ingested utilizing oral, combustion, or vaporization delivery.

Tobacco alternative: May also comprise substitute herbal tobacco products such as corn silk, mint, cinnamon, lemongrass, clover, bugasse, and shisha, among others, comprising nicotine, nicotine salts, or nicotine derivatives, which are often mixed or flavored with various fruit flavors, energy drink flavors, or other appealing flavors and which may produce byproducts that can be ingested utilizing oral, combustion, or vaporization delivery.

Treat: Is generally intended to mean providing an alternate remediation to a tobacco product to a subject. Providing a remediation to act upon a subject by providing an agent intended to be a substitute for a tobacco product.

Treat: May also mean substitution of a first tobacco product with a second tobacco product, wherein the second product has a preferable risk profile, i.e.: substitution of a tobacco product which utilizes combustion with a tobacco or nicotine product which does not utilize combustion or which utilizes vaporization.

Validate/Validation: Is intended to mean a procedure for checking that a product, service, or system has met the needs or requirements of the stakeholder(s), and is typically done in the later phases of product, process, or system development to assure that the development and verification procedures for a product, service, or system result in a product, service, or system that meets initial requirements, specifications and regulations.

Vapor/vaporize/vaporization: Is intended to mean converting a normally liquid or solid substance into an aerosol, gaseous or semi-gaseous state, where it is diffused or suspended in the air; i.e.: haze, mist, or steam. Vaporization is also defined as the process for producing a gaseous by-product that is produced from a normally liquid or solid state material, at a temperature which is below the combustion temperature of said material.

Verify/verification: Is intended to mean a procedure for checking that a product, service, or system complies with a regulation, requirement, specification, or imposed condition; e.g.: has met an initial set of requirements, specifications or regulations and typically performed in the initial or development phases of product, process, or system development.

Figure 1B:
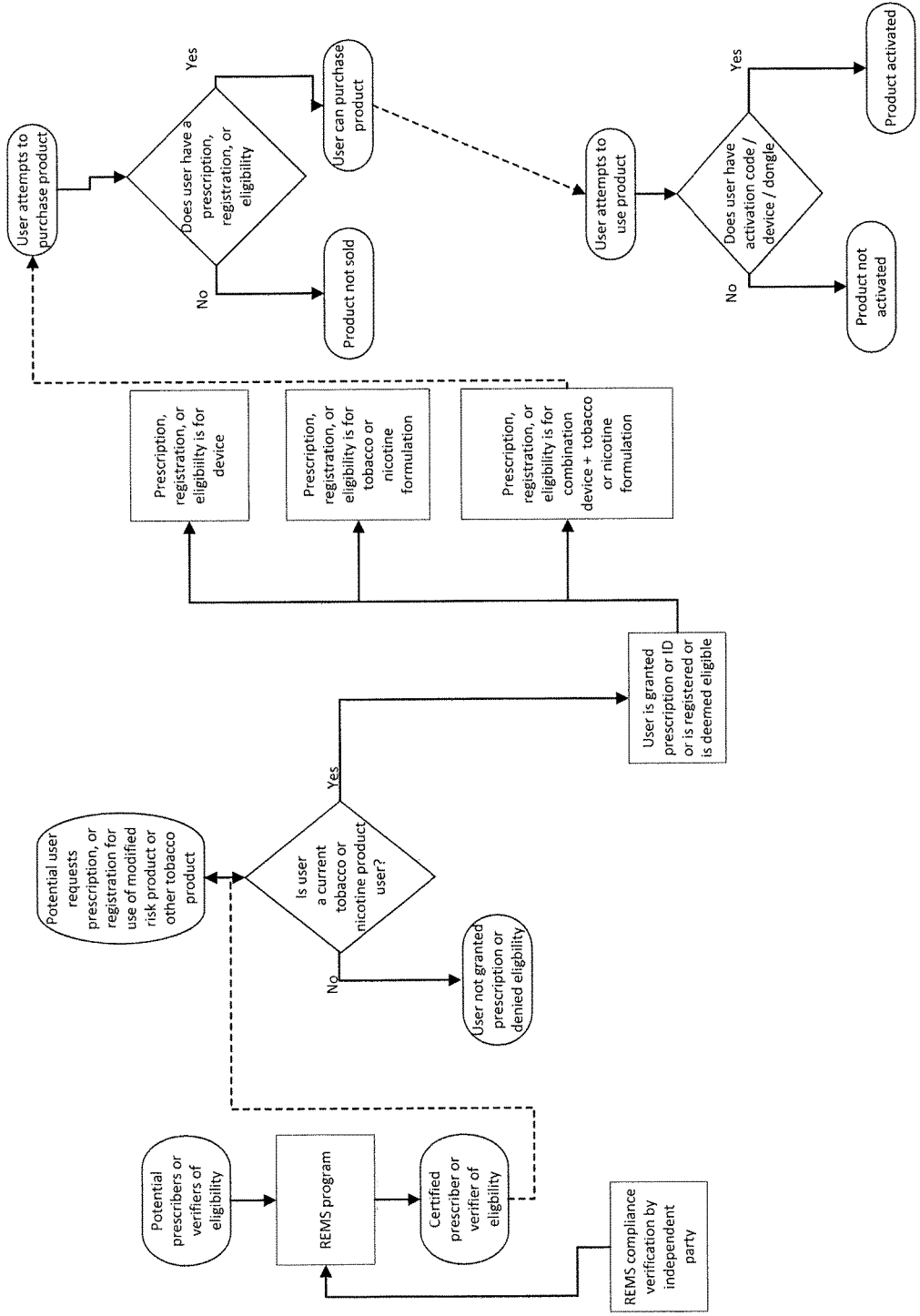
FIG. 1B illustrates another possible configuration of an overall Risk Evaluation and Mitigation Strategy (REMS) where a subject has not used a nicotine replacement therapy.

Methods:

Provided herein are methods of protecting the public health by increasing the likelihood that a subject addicted to a tobacco product will stop using a tobacco product wherein the subject has previously failed to stop using a tobacco product by other means. Such methods may include the use of controlled Risk Evaluation and Mitigation Strategies (REMS) such as that illustrated in FIGS. 1A & 1B. These REMS may be applied to drugs, biologics, devices, or combination devices that include any two or more of these things. REMS are intended to answer the question: "Do the benefits of the drug, biologic, (and/or device) outweigh the risks?" Some of the factors taken into consideration include:
Seriousness of the disease or condition to be treated
  Size of the patient population;
  Expected benefit of the drug or biologic (and/or device);
  Expected duration of treatment;
  Seriousness of the known or potential adverse events.

These evaluations are performed not only prior to the approval of a new drug, biologic, (and/or device), in this case, a modified risk product or other tobacco product device for delivering nicotine, but also throughout the entire life cycle of the drug, biologic and/or device. This serves as a means to continuously assess the safety and efficacy of existing products based on adverse event reports and results from post-marketing clinical studies.

For every drug, biologic and/or device approved by the FDA, the risks associated with its use are communicated through the product package insert. In some cases, however, the manufacturer and/or the FDA may determine that expanded REMS are necessary to go beyond product labeling in order to manage risks and thereby ensure that the benefits outweigh the risks.

Figure 2:
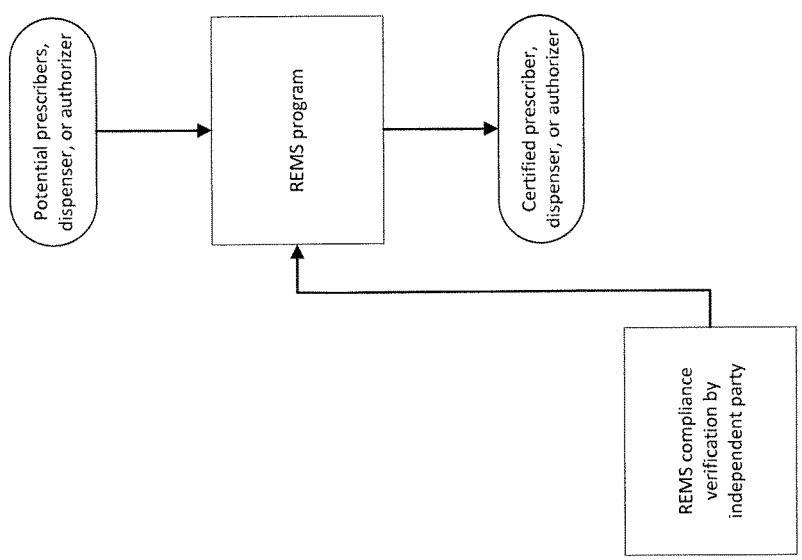
FIG. 2 illustrates a possible configuration of a REMS component program for the authorization, verification and program compliance of qualified prescribers and dispensers of modified risk products or other tobacco products.
Figure 3B:
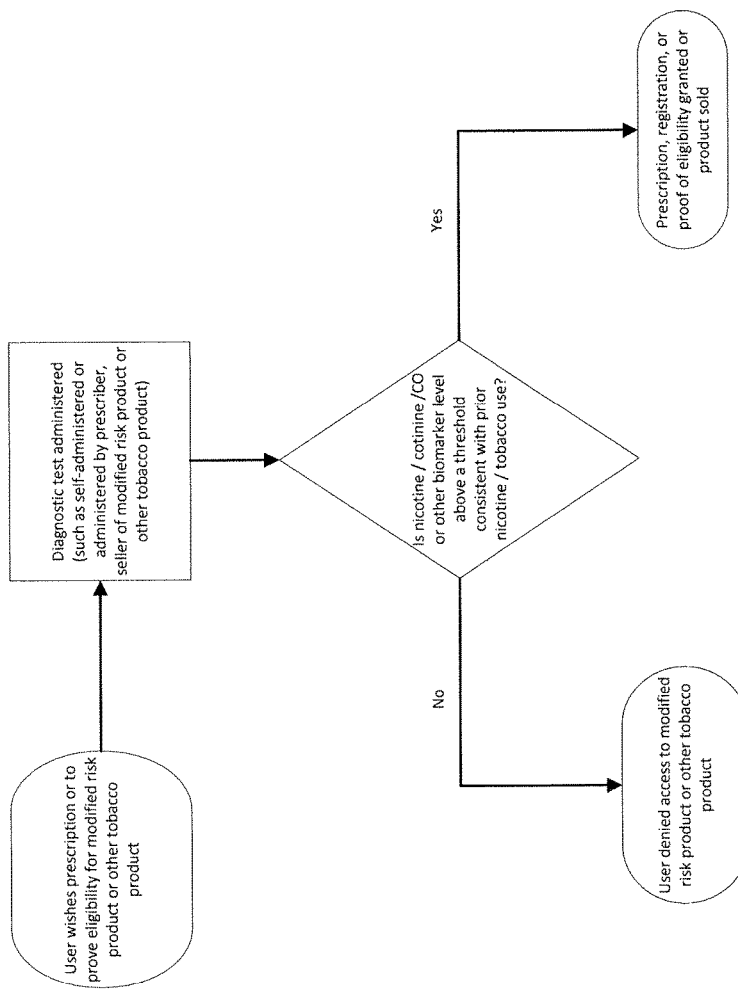
FIG. 3B illustrates a possible configuration of a REMS component program for the authorization and dispensation of prescriptions for a Modified Risk Product or other tobacco product when a subject has previously not used a nicotine replacement therapy.
Figure 3C:
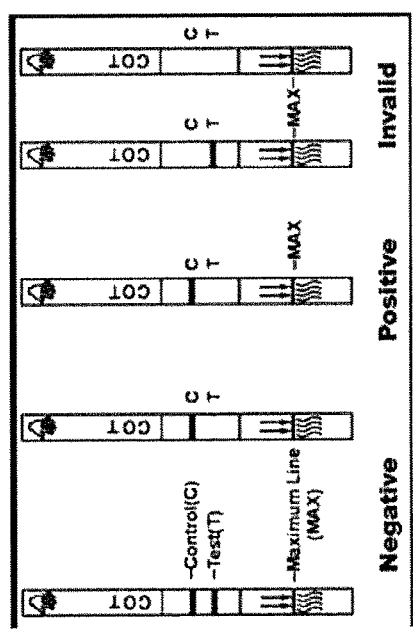
FIG. 3C illustrates a representative test strip for verification of nicotine presence in a subject's system.
Figure 3D:
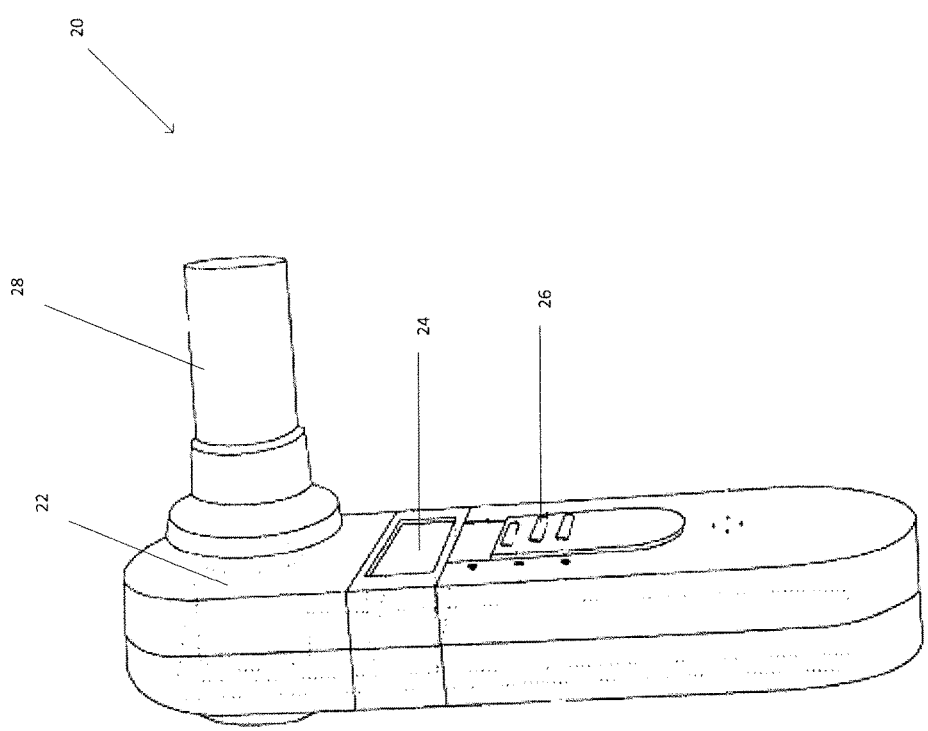
FIG. 3D illustrates an exemplary carbon monoxide monitor for verification of a subject's prior tobacco use.
Figure 6:
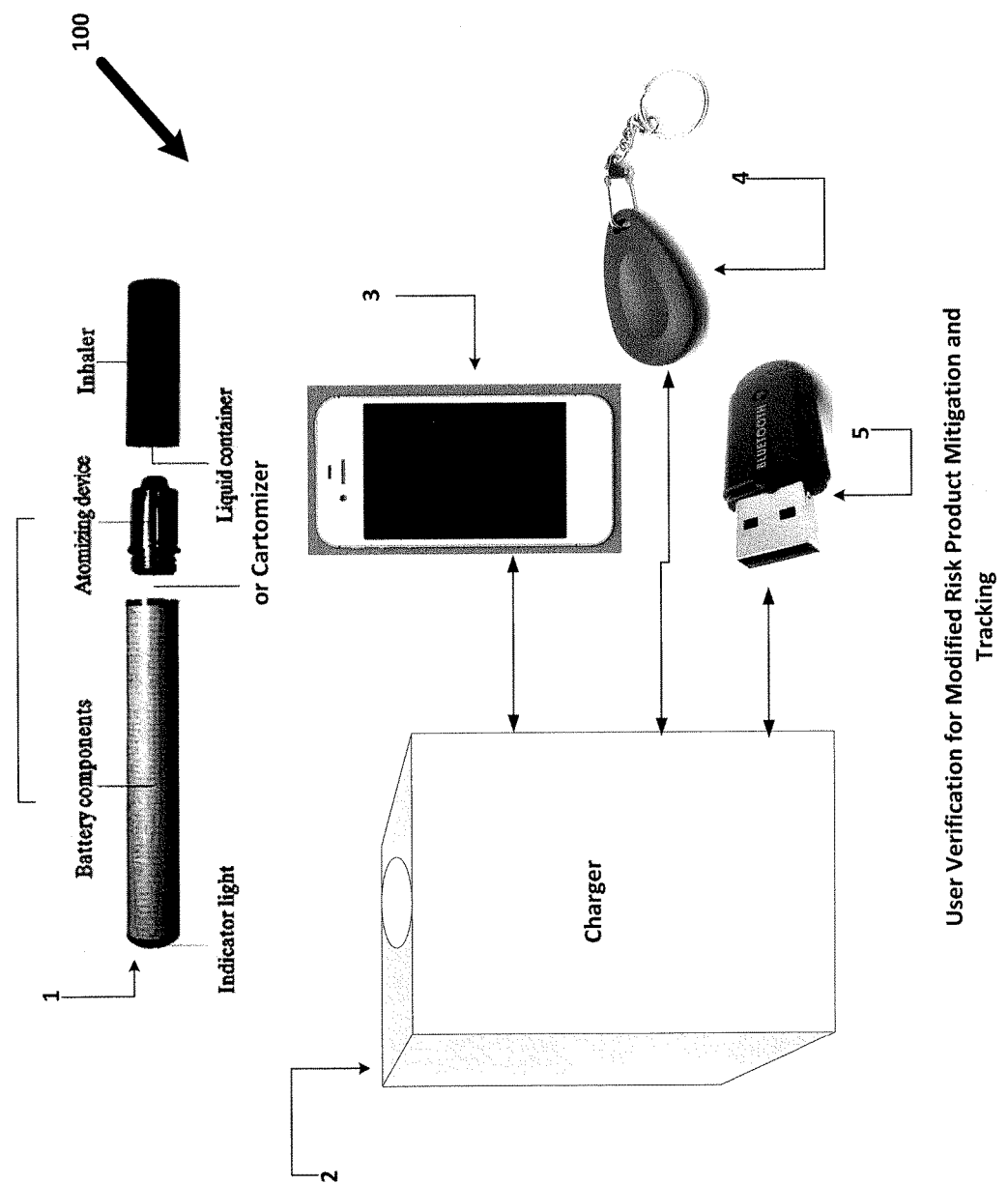
FIG. 6 illustrates a possible configuration of a REMS component program for User Verification, Tracking, and Automated Reporting Method of a Modified Risk Product or other tobacco product and also illustrates a possible system for verification, tracking, and reporting use of, and or subject compliance for the use of a Modified Risk Product.
Figure 7A:
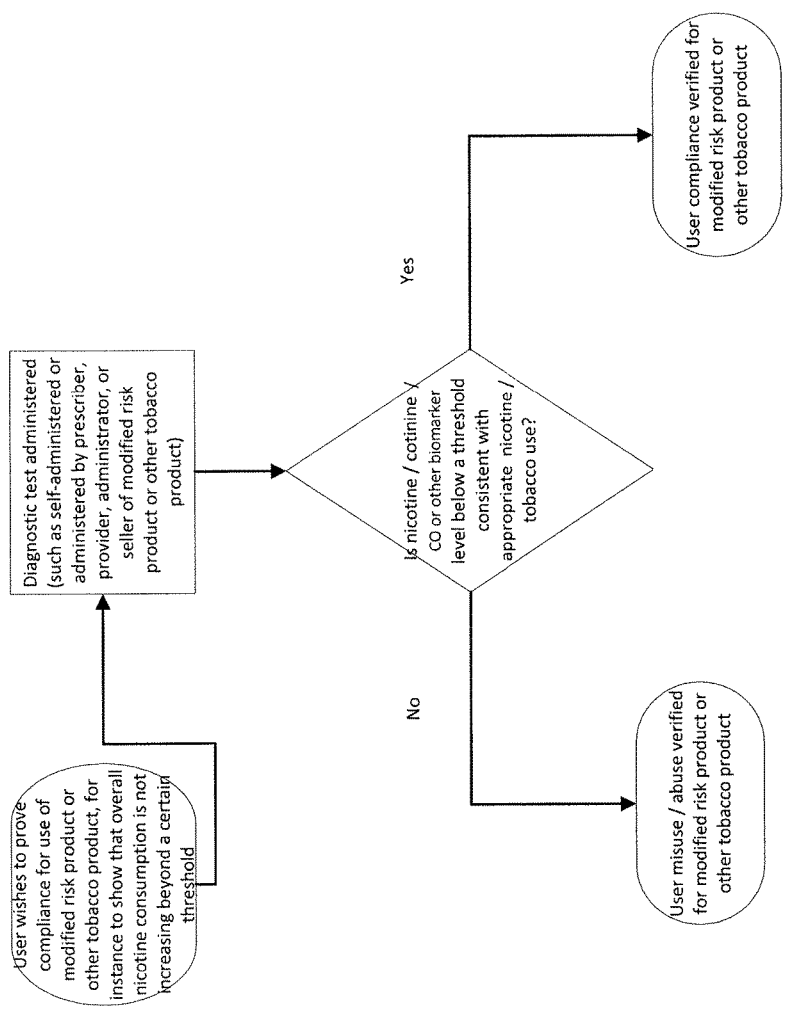
FIG. 7A illustrates a possible configuration of a REMS component program for User Eligibility for, or User Compliance of, a Modified Risk Product or other tobacco product.
Figure 7B:
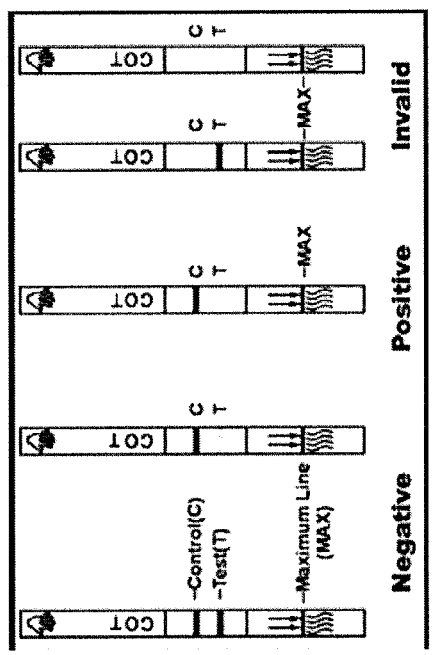
FIG. 7B illustrates a representative test strip for verification of nicotine presence in a subject's system which could be adapted for use in a REMS program for User Compliance or testing for misuse or abuse of a Modified Risk Product or other tobacco product.

As illustrated in FIGS. 1 & 2, elements of a REMS program for Nicotine Replacement Therapy (NRT) may include Elements to Assure Safe Use, (ELASU). A Nicotine REMS program as proposed herein is likely to comprise several algorithms including:

1. A Prescriber/Dispenser Authorization Algorithm (FIG. 2): which may include;
    Specific personnel authorized by statute to prescribe or dispense a Modified risk product or other tobacco product
    A defined Risk Evaluation and Mitigation Strategy for the specific Modified risk product or other tobacco product
    An auditing and certification program to verify that qualified prescribers/dispensers are appropriately trained and following the REMS protocols for verification and dispensation of Modified risk products or other tobacco products
2. A Prescription Process and Verification Algorithm (FIGS. 3A & 3B): which may include;
    A method for verifying that only qualified subjects receive a Modified risk product or other tobacco product, which may include one or more of the following:
        i. evidence of meeting a minimum age requirement;
        ii. evidence of a previously failed nicotine replacement therapy;
        iii. evidence of a at least one failed attempt by the patient to quit using such tobacco product;
        iv. collecting samples and measuring nicotine levels, nicotine levels, CO levels, or other biomarker levels in blood, expelled breath, saliva, hair, or urine to verify that the subject's nicotine or nicotine by-product levels, nicotine levels, CO levels, or other biomarker levels are above or consistent with levels expected for a tobacco or nicotine user; (FIG. 3C)
        v. a prescription from a physician or accredited healthcare provider;
        vi. electronic or telephonic verification of a unique subject eligibility card or code identifier;
        vii. software verification of a unique subject eligibility card or code identifier;
        viii. electronic fingerprint verification of an eligible subject;
        ix. an activation code;
        x. an electronic dongle; and
        xi. an electronic security key fob, or equivalent.
    A process for dispensing the Modified risk product or other tobacco product which may include;
        i. Directly providing a dispensing modified risk device and/or a modified risk tobacco/nicotine product
        ii. Registration in a REMS program
3. A User Purchasing Verification Algorithm (FIG. 4): which may include;
    A method for verifying that a qualified subject may purchase a modified risk product or other tobacco product from an authorized distributor, which may include one or more of the following:
  i. evidence of meeting a minimum age requirement;
  ii. evidence of a previously failed nicotine replacement therapy;
  iii. evidence of a at least one failed attempt by the patient to quit using such tobacco product;
  iv. collecting samples and measuring nicotine levels, nicotine levels, CO levels, or other biomarker levels in blood, expelled breath, saliva, hair, or urine to verify that the subject's nicotine or nicotine by-product levels, nicotine levels, CO levels, or other biomarker levels are above or consistent with levels expected for a tobacco or nicotine user;
  v. a prescription from a physician or accredited healthcare provider;
  vi. electronic or telephonic verification of a unique subject eligibility card or code identifier;
  vii. software verification of a unique subject eligibility card or code identifier;
  viii. electronic fingerprint verification of an eligible subject;
  ix. an activation code;
  x. an electronic dongle; and
  xi. an electronic security key fob, or equivalent.
4. A Product User Verification (FIG. 5): which may include;
  A method or process for verifying a subject is authorized to use a Modified risk product or other tobacco product before a product will be activated or function; which may include one or more of the following:
    i. software verification;
    ii. card or code identifier;
    iii. electronic fingerprint verification of an eligible subject;
    iv. lip print verification of an eligible subject;
    v. a special article of clothing;
    vi. an activation code;
    vii. an electronic ring;
    viii. an electronic dongle; and
    ix. an electronic security key fob, or equivalent.
5. A User Verification and Mitigation Tracking System (FIG. 6): which may include;
  A Modified Risk System (100) comprising: one or more of the following:
    i. an electronic cigarette; (1)
    ii. an electronic pipe;
    iii. an electronic cigar;
    iv. an electronic water pipe; or
    v. an electronic vaporizer (1), and also comprising one or more of the following:
      1. a battery, an atomizer or cartomizer, electronic circuitry, a memory storage device for tracking component usage activity, a means of memory transfer, and a charging circuit;
    vi. a charger base station (2) comprising one or more of the following:
      1. a memory storage device; a means for receiving data and transmitting said data from said modified risk product or other tobacco product memory storage device to a third party;
    vii. an identification recognition system;
    viii. activation software for recognition of a specific device keyed to said charger base and capable of interfacing with an external device, wherein said external device comprises one or more of the following:
      ix. a smart phone (3); a computer; an electronic fob (4); an electronic dongle; a ring; an article of clothing; and a wireless communication device (5).
6. A REMS Compliance Program (FIG. 7A): which may include;
  A method of testing to confirm that a subject is complying with (and not misusing or abusing) the Modified risk product or other tobacco product.
    i. Testing strips, CO level, or other methods of compliance verification (FIGS. 7B and 3D).

Described herein are methods of: (1) increasing the likelihood that a subject will stop using a tobacco product or tobacco alternative; and (2) decreasing the likelihood that a subject not using a tobacco product will start using the tobacco product. The methods include providing a modified risk product or other tobacco product, such as a device for administration of nicotine in a vapor form, if the subject: (1) has previously failed a nicotine replacement therapy; (2) had a failed attempt to quit using the tobacco product; (3) has a prescription or other verification mechanism indicating eligibility for purchase or use of the modified risk product or other tobacco product.

Provided herein is a method of protecting public health comprising: increasing the likelihood that a first subject or a second subject will stop using a tobacco product or tobacco alternative product by providing a modified risk product or other tobacco product such as a device for administration of nicotine in a vapor form to a first subject addicted to the tobacco product wherein the first subject has previously failed a nicotine replacement therapy. It is generally understood that there are numerous recognized therapies intended to reduce the use of tobacco and/or bring about the cessation of addiction to tobacco products and in particular, nicotine. These include; abstinence, nicotine gum, nicotine oral spray, nicotine inhaler, nicotine nasal spray, nicotine lozenge, nicotine dermal patch, Bupropion®, Chantix®, or similar medications and oral nicotine replacement products. In many cases, these products or methods fail. The applicant believes that by combining a REMS program with their Modified risk product or other tobacco product, the user will be more likely to switch to a preferred form of nicotine delivery which has a preferable risk profile, while also minimizing the risk that non-tobacco users will initiate use of the modified risk product or other tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a REMS typically involving one or more of the following components; subject eligibility verification, subject compliance verification to a risk mitigation strategy, and overall validation of the success of said risk evaluation and mitigation strategy.

Among the methods included in the REMS are methods wherein the product is prescribed, provided, or a subject's eligibility is verified by a physician, a nurse, a pharmacist, or an accredited healthcare provider. FIG. 3A illustrates one embodiment of a method wherein the potential subject may request a prescription for a controlled product from a qualified, accredited healthcare provider, who verifies that the subject is qualified to receive said product, prior to issuing a prescription. A subject may be a current tobacco or nicotine user who may have previously tried and failed a nicotine replacement therapy.

Alternatively, the product may be regulated as an over the counter (OTC) or retail product, wherein the subject may self-subscribe and acquire the product by personally requesting it from a qualified individual, authorized to dispense said product, upon proof or verification of eligibility to acquire said product, such as proof of a minimum age requirement, etc. FIG. 3B illustrates another embodiment of a method wherein the potential subject may request an FDA designated modified risk tobacco product or a tobacco alternative product which may include a non-combustion or vaporization-based delivery of nicotine or tobacco from a qualified, accredited healthcare provider, or employee of a convenience or retail store, who verifies that the subject is qualified to receive said product. A subject may be a current tobacco or nicotine user who may or may not have previously tried and failed a nicotine replacement therapy. A simple nicotine test strip may be all that is required for this verification. Alternately, verification may require more complex tests comprising: blood, expelled breath, hair, or urine taken for analysis.

In some embodiments, the devices and methods of using the modified risk product or other tobacco product may be provided by, or subject eligibility verified by, an accredited employee of a convenience or retail store or by an employee of an accredited convenience or retail store.

In still other situations, the product is prescribed, provided, and or subject eligibility verified by an internet or wireless based application, service or business. While in still other situations the product may be prescribed, provided, or subject eligibility verified by a call center or phone based application service or business. The use of Skype or other real time phone and internet services makes these verification and prescribing services possible.

In any of the preceding examples, the prescribers or providers of the modified risk product or other tobacco product have been qualified to deliver said modified risk product or other tobacco product through a REMS compliance verification program as illustrated in FIG. 2, which is typically administered and controlled by a qualified independent party having full authorization to qualify said providers and/or their employees and to audit their internal systems for recordkeeping. Either the facility employing the prescribers or providers or the individual prescribers or providers themselves may be qualified and audited.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples taken before (and/or in some variations, after) being provided a modified risk product or other tobacco product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the risk evaluation and mitigation strategy (REMS) may incorporate a means of subject compliance verification and or the subject's eligibility to participate in a REMS program and have a modified risk product or other tobacco product prescription. Subject compliance is commonly used in clinical drug studies to verify the concentration levels and patient compliance to protocols, among other clinical study outcome measures. FIG. 7 illustrates one possible configuration for such a REMS program wherein a subject's eligibility to participate in a program is first verified prior to being given a prescription, and the subject may be tested again at a later date to demonstrate program compliance.

In other embodiments, the compliance verification or the REMS program validation may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine or tobacco products in the market.

Some aspects of these methods may require physical tests that must be performed to provide accurate and quantifiable data wherein the subject must present themselves to a qualified individual in order for the test to be completed. In some embodiments, the subject compliance verification or the REMS program validation testing is performed by a physician, a nurse, a pharmacist, a phlebotomist, or an accredited healthcare provider and the samples obtained are sent to a qualified lab for analysis.

In other embodiments, subject compliance verification is performed by an accredited employee of a convenience or retail store, or an employee of an accredited convenience or retail store. Such compliance tests would comprise verification of subject identity and collection of saliva, hair, urine, or breath samples, which could be forwarded to a qualified lab for analysis.

Alternatively, subject compliance or the REMS program validation may be measured passively through the use of electronic technology. One such example of this is illustrated in FIG. 6. In this example, a device that is a component of modified risk system, may comprise an electronic cigarette, an electronic pipe, an electronic cigar, an electronic water pipe, or an electronic vaporizer for delivering a nicotine-containing vapor, comprising a battery, an atomizer, electronic circuitry, a memory storage device for tracking components of usage activity, a means of memory transfer, and a charging circuit, along with a charger base station comprising a memory storage device, a means for receiving data from said component device memory storage device and then having the ability to transmit said data to a third party which passively monitors the device and indirectly, the subject for compliance based on the transmitted data.

The component device and the charging base would be configured such that activation software would be required for recognition of the specific device, keyed to said charger base. This software could be embedded and matched to each component set in a modified risk product or other tobacco product, and be capable of interfacing with an external device, wherein said external device comprises; a smart phone, computer, electronic fob, electronic dongle and a Bluetooth or wireless communication device, which would need to be within a fixed range for activation and continued use.

Alternatively, the components could be configured with a programmable code which must be entered periodically for activation. Still further the components could be hard wired with a timing circuit that requires periodic physical contact between the components for activation.

In addition, the transmission of collected data could occur over the internet via a hardwired or wireless connection through a base computer device for analysis and validation by an accredited healthcare professional or REMS monitor or administrator.

Provided herein is a method of protecting public health comprising: increasing the likelihood that a first subject or a second subject will stop using a tobacco product by providing a modified risk product or other tobacco product for administration to the first subject addicted to the tobacco product only after at least one failed attempt by the first subject to quit using such tobacco product. These modified risk products or other tobacco products comprise an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

The previously failed attempt to quit using a tobacco product commonly comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments of the method, the product is prescribed, provided, administered, or a subject's eligibility is verified by a physician, a nurse, a pharmacist, or an accredited healthcare provider, as illustrated in FIG. 3.

In other embodiments, the product, which may be an OTC product, is provided, administered, or subject eligibility verified by an accredited employee of a convenience or retail store. In still other embodiments, the product is provided, administered, or a subject's eligibility is verified by an employee of an accredited convenience or retail store.

In still other embodiments, the product which may be either a prescription or OTC product, is provided, administered, or a subject's eligibility is verified by an internet or wireless based application, service or business. In still other embodiments of the method the product is provided, administered, or a subject's eligibility is verified by a call center or phone based application service or business, using Skype or other real time phone and internet services.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

In some embodiments, the risk evaluation and mitigation strategy incorporates a means of subject compliance verification.

In some embodiments, the subject compliance verification comprises collecting and sending samples taken before (and/or in some variations, after) being provided a modified risk product or other tobacco product, for analysis to an accredited testing facility, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

Provided herein is a method of protecting public health comprising increasing the likelihood that a first subject or a second subject will stop using a tobacco product by providing a modified risk product or other tobacco product for administration to the first subject addicted to the tobacco product, only after the modified risk product or other tobacco product is prescribed to the first subject or the first subject is otherwise verified as eligible to purchase or use the product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, or verification of a prior nicotine replacement therapy.

Referring to FIG. 3B, in some embodiments, the subject eligibility verification includes administering a diagnostic test. For example, the diagnostic test can include collecting samples and measuring nicotine or other by-product of tobacco use, such as cotinine, levels in blood samples, expelled breath samples, saliva samples, hair samples, and in urine samples to verify that the subject's nicotine or nicotine by-product levels are above or consistent with levels expected for a tobacco or nicotine user. As shown in FIG. 3C, a nicotine or cotinine test can determine whether the subject is positive or negative for tobacco. In some embodiments, a cotinine concentration of greater than 7 ng/ml, greater than 8 ng/ml, greater than 10 ng/ml, or greater than 12 ng/ml in a subject's saliva can be used to identify a user of tobacco. Likewise, a cotinine concentration of greater than 35 ng/mL, greater than 40 ng/mL, greater than 42 ng/mL, or greater than 49 ng/mL in a subject's urine can be used to identify a user of tobacco.

Another example of a diagnostic test for subject eligibility verification is a breath carbon monoxide (CO) test. The breath carbon monoxide test can be administered, for example, with a carbon monoxide breath monitor 20 as shown in FIG. 3D. In some embodiments, the monitor can be handheld. The carbon monoxide monitor 20 can include a sensor 22, such as an electrochemical gas sensor, and a mouthpiece 28 for the subject to expel air through. The sensor 22 can be used to detect the carbon monoxide in parts per million (ppm). In some embodiments, a CO concentration of greater than 5 ppm, greater than 6 ppm, greater than 8 ppm, or greater than 10 ppm can be used to identify a user of tobacco, e.g. a user of combustible tobacco. For example, the minimum threshold level can be between 3-5 ppm, between 5-10 ppm, or greater than 10 ppm. In some embodiments, the CO level in a user's blood can be used to determine whether the user has ingested tobacco. The carbon monoxide test can advantageously detect CO when someone ingested tobacco within 10 hours before the test, such as within 8 hours or within 6 hours. Likewise, the carbon monoxide test can detect when someone has ingested tobacco regularly such that CO has built up a reservoir in their blood or lungs. In some embodiments, the carbon monoxide test can be given in the morning (such as within 4 hours of the subject awaking), as regular tobacco users tend to use tobacco within several hours of waking. Further, the carbon monoxide test can be used to determine whether the subject is a light or heavy smoker. For example, a reading of between 6 and 10 ppm can indicate a light user, and a reading of greater than 10 ppm can indicate a heavy user. In some embodiments, eligibility verification can be provided only for heavy users.

Any of the diagnostic tests described herein can also include a mechanism to exclude or select for users who have particular smoking, cardiovascular, or respiratory diseases or conditions, such as asthma or chronic obstructive pulmonary disease (i.e., the eligibility verification can be negative such that the user cannot obtain the modified risk product). For example, the diagnostic test can include a nitric oxide (NO) breath analysis to eliminate or select for these subjects.

It is to be understand that additional diagnostic tests can also be used to determine if the subject is a tobacco user, such as tests for thiocyanate, 4-Aminobiphenyl-hemoglobin adduct, Benzo[a]pyrene-DNA adduct, PAH-albumin adduct, urinary tobacco-specific nitrosoamines, urine hyroxyproline, and/or urine mutagenicity levels in the subject. Exemplary cut-off levels for various diagnostic tests (i.e. a measured level above the cut-off value indicates a tobacco user eligible for use of the modified risk product) are included in FIG. 3E.

In some embodiments, when a diagnostic test is used to determine eligibility verification, the readings can be displayed on the device itself. For example, the specific readings (e.g., ppm of CO) can be indicated on a display of the device, such as the display 24 of device 20 or an indication of passing the cut-off value (e.g., a particular light 26 or the word "pass" on the display 24 of the device 20) can be indicated on the monitor or device. In other embodiments, when a diagnostic test is used, the results can be processed by a third party, e.g., the device or readings from the device can be passed onto a third party to determine whether the subject is eligible for the modified risk product.

Once the subject is verified as eligible (e.g., based upon the results of the diagnostic test or prescription by a physician or healthcare provider), the verified subject can be provided with evidence of eligibility for purchase or use of the modified risk product. For example, subject may be provided with an electronic or telephonic verification of a unique subject eligibility card or code identifier, software verification of a unique subject eligibility card or code identifier, electronic fingerprint verification, an activation code, entry into a database, or an electronic dongle, electronic security key fob, or the equivalent.

In some embodiments, components of the subject eligibility verification may be performed by a physician, a nurse, a pharmacist, an accredited healthcare provider, or an employee of a convenience or retail store. In some embodiments, components of the subject eligibility verification can be self-administered.

In some embodiments, the risk evaluation and mitigation strategy incorporates a means of subject compliance verification. In some embodiments, the subject compliance verification comprises collecting and sending samples taken before (and/or in some variations, after) being provided a modified risk product, for analysis to an accredited testing facility, and measuring the difference between samples for nicotine levels in blood, expelled breath, saliva, hair, and in urine. In some embodiments, components of the subject compliance verification may be performed by a physician, a nurse, a pharmacist, an accredited healthcare provider, or an employee of a convenience or retail store. In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require phyisical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider. In other embodiments, subject compliance verification is performed by an employee of a convenience or retail store.

Figure 5:
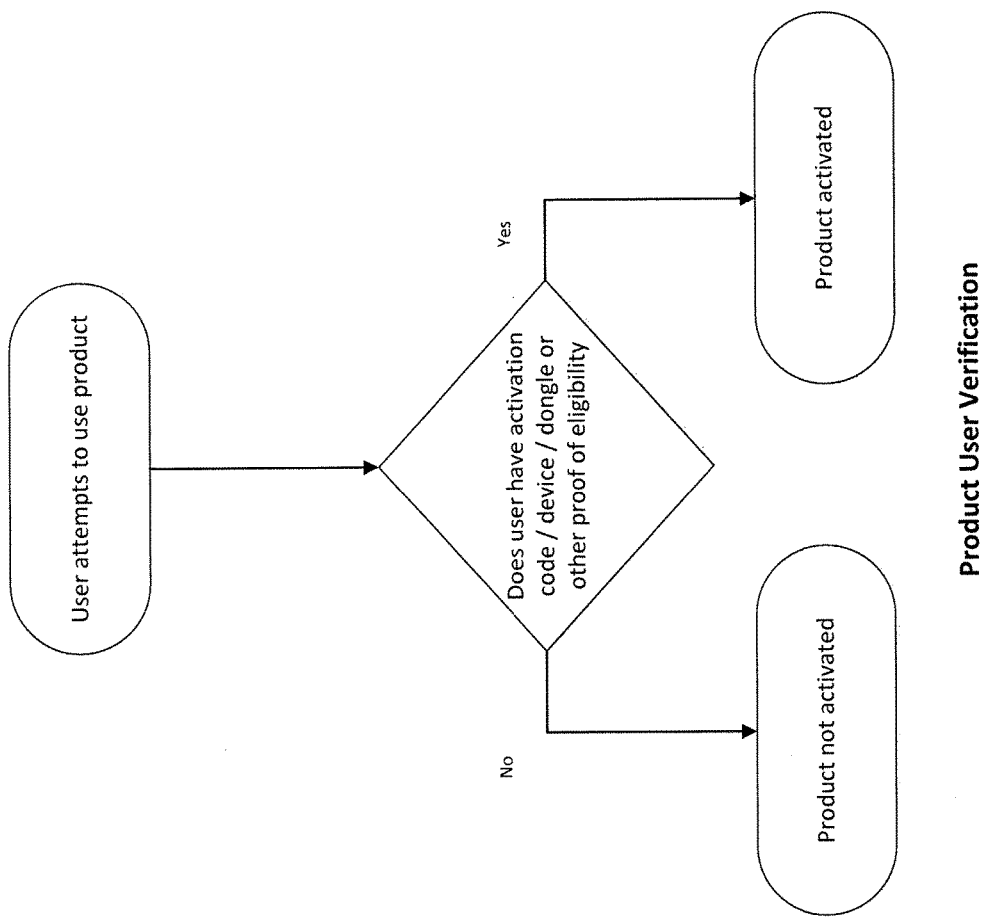
FIG. 5 illustrates a possible configuration of a REMS component program for User Verification of a Modified Risk Product or other tobacco product.

Referring to FIG. 5, in some embodiments, the device itself can include a diagnostic test for verification eligibility. For example, the modified risk product or other tobacco product can include a CO breath analysis sensor directly on the device, such as on the mouthpiece of the modified risk product, that only allows use of the device if the user is verified as a user of tobacco (e.g. has a CO level of above a particular amount as described above, including above average values for a non-tobacco user).

Examples of sensors and sensor technologies that may be used may include electrochemical and Metal oxide semiconductor (MOS) sensors. An electrochemical sensor may produce a current that is related to the target gas concentration around a sensor. For example, an electrochemical cell may be used, to provide a highly accurate and linear output to carbon monoxide concentration, requiring minimal power, and has a long lifetime (e.g., 5 years or greater). MOS (Metal oxide semiconductor) are typically low cost, small size and may provide superior performance. For example, the Figaro TGS5342 electrochemical sensor is 15 mm diameter, 27.9 mm length, however similar sensors may be smaller. In particular, sensors configured to operate as a gating/enabling tool for use of any of the devices (e.g., modified risk products or other tobacco products) described herein may be specifically adapted to sample a patient's breath before they can operate the device. Once the sensor has confirmed that the CO level is above a naïve threshold (e.g., a threshold of CO levels for non-smokers, and/or those who have not used modified risk products or other tobacco products before), the device may be enabled for operation for some amount of time (e.g., seconds, minutes, hours). Other examples of sensors may include SGX sesnortech (E.g., EC4-2000-CO and MICS-4514 MOS sensors), Figaro TGS3870 MOS sensors, and the like.

Provided herein is a method of protecting public health comprising decreasing the likelihood that a second subject not using a tobacco product will start using the tobacco product by providing a modified risk product or other tobacco product for administration to the first subject addicted to the tobacco product wherein the first subject has previously failed nicotine replacement therapy.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy. In some embodiments, the previously failed attempt to quit using said tobacco product comprises abstinence, nicotine gum, nicotine oral spray, nicotine inhaler, nicotine nasal spray, nicotine lozenge, nicotine dermal patch, Bupropion, Chantix, or comparable oral nicotine replacement product.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, and/or verification of a previously failed prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user.

Figure 4:
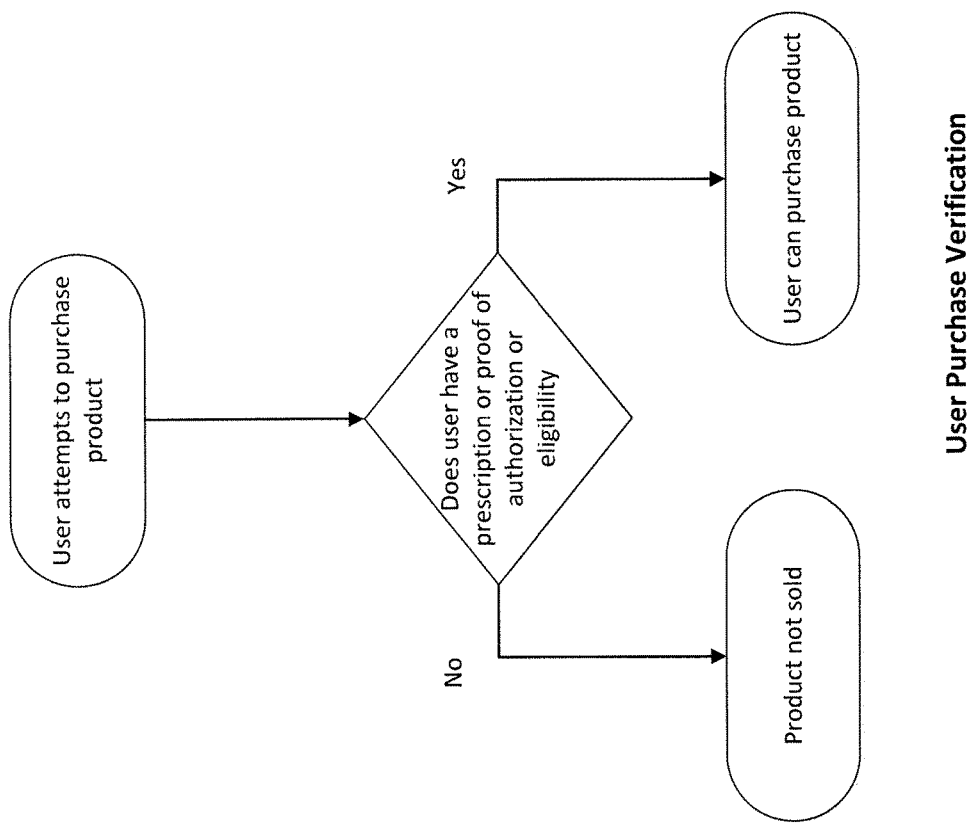
FIG. 4 illustrates a possible configuration of a REMS component program for the purchase of Modified Risk Products or other tobacco products.

One such mitigation strategy is illustrated in FIG. 4. As illustrated herein, the subject attempting to purchase or acquire a controlled modified risk product or other tobacco product would provide some form of qualified proof that verifies they are qualified to obtain said Modified risk product or other tobacco product and participate in the REMS. This purchase verification requirement would typically comprises, a prescription for a controlled substance in addition to a formal verification of subject identity which may comprise a fingerprint, facial recognition, retinal scan, or other biometric identification. Alternatively the identification and verification may comprise having the subject providing a code, a dongle, an electronic FOB, or web registration, to name but a few methods.

In some embodiments, the product is provided or a subject's eligibility is verified by a physician, a nurse, a pharmacist, an accredited healthcare provider, an accredited employee of a convenience or retail store, or an employee of an accredited convenience or retail store.

In some embodiments, the product is prescribed, provided, or subject eligibility verified by an internet or wireless based application, service or business, or by a call center or phone based application service or business. The use of Skype or other real time phone and internet services makes these verification and prescribing services possible.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

Provided herein is a method of protecting public health comprising decreasing the likelihood that a second subject not using a tobacco product will start using the tobacco product by providing a modified risk product or other tobacco product for administration to the first subject addicted to the tobacco product only after at least one failed attempt by the first subject to quit using such tobacco product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, and overall validation of the success of said risk evaluation and mitigation strategy.

In some embodiments, the previously failed attempt to quit using said tobacco product comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is prescribed, provided, or subject eligibility verified by a physician, a nurse, a pharmacist, an accredited healthcare provider, an accredited employee of a convenience or retail store, or by an employee of an accredited convenience or retail store.

In some embodiments, the product is prescribed, provided, or subject eligibility verified by an internet or wireless based application, service or business, or by a call center or phone based application service or business. The use of Skype or other real time phone and internet services makes these verification and prescribing services possible.

In other embodiments, the product, which may be an OTC product, is provided, administered, or a subject's eligibility is verified by an accredited employee of a convenience or retail store, or by an employee of an accredited convenience or retail store.

In still other embodiments, the product which may be either a prescription or OTC product, is provided, administered, or a subject's eligibility is verified by an internet or wireless based application, service or business, or by a call center or phone based application service or business, using Skype or other real time phone and internet services.

In some embodiments, the subject eligibility verification comprises providing a prescription from an accredited healthcare provider, verifying a subject's identity, a minimum age for eligibility, or verification of a prior nicotine replacement therapy.

In other embodiments the subject eligibility verification may comprise having the subject provide an electronic or telephonic verification of a unique subject eligibility card or code identifier, software verification of a unique subject eligibility card or code identifier, electronic fingerprint verification, an activation code, or an electronic dongle, electronic security key fob, or the equivalent.

In some embodiments, the subject eligibility verification comprises collecting samples and measuring nicotine levels, nicotine levels, CO levels, or other biomarker levels in blood samples, expelled breath samples, saliva samples, hair samples, and in urine samples to verify that the subject's nicotine or nicotine by-product levels, nicotine levels, CO levels, or other biomarker levels are above or consistent with levels expected for a tobacco or nicotine user. If a second subject has not been using a tobacco product or alternative tobacco product comprising nicotine, such samples would be negative and disqualify said second subject from obtaining a modified risk under this criteria.

As previously described, another method of decreasing the likelihood that a second subject not using a tobacco product, will start using the tobacco product after a first addicted subject is prescribed a modified use product after a previously failed attempt to quit, could comprise the passive use of electronic technology. One such example of this is illustrated in FIG. 5. In this example, a device that is a component of a modified risk system, may comprise an electronic cigarette, an electronic pipe, an electronic cigar, an electronic water pipe, an electronic vaporizer, and/or a tobacco or nicotine product, for delivering a nicotine-containing vapor, comprising a battery, an atomizer, electronic circuitry, a memory storage device for tracking various aspects of component usage activity, a means of memory transfer, and a charging circuit, along with a charger base station comprising a memory storage device, a means for receiving data from said component device memory storage device and comprising the means to transmit said data to a third party which passively monitors the device and indirectly, the subject, for compliance to the REMS based on the transmitted data.

The component device would be configured such that activation software acting as a user identification system would be required for recognition of the specific device, keyed to said charger base. This software could be embedded and matched to each component set in a modified risk product, and be capable of interfacing with an external device, wherein said external device comprises; a smart phone, computer, electronic fob, electronic dongle, a special ring, and/or a Bluetooth or wireless device, which would need to be within a fixed range for activation and continued use.

Alternatively, the device could be configured to have a fingerprint or lip print reader on the body or mouthpiece that is matched to the first subject.

Alternatively a special ring or wrist band worn on the hand of the first subject or other article of jewelry could provide a user identification system and be configured to mate with the device, wherein the device will only activate if it is in the immediate proximity of the subject's hand.

In any of the prior examples, the devices could be configured with proximity sensors requiring the subject to be within a fixed distance such as 20 feet, or ten feet, or more preferably within five feet or less.

Alternatively, the components could be configured with a programmable code which must be entered periodically for activation. Still further the components could be hard wired with a timing circuit that requires a minimal period of time between uses for activation.

In addition, the device could be configured as shown in FIG. 6 with a base having hardware and software for the transmission of collected data as previously described. In this example, the modified risk product or other tobacco product configuration could be used for user verification, user compliance, or even validation of a REMS for a modified risk product.

Provided herein is a method of protecting public health comprising decreasing the likelihood that that a subject not using a tobacco product will start using the product by providing a modified risk product or other tobacco product for administration to the first subject addicted to the tobacco product, only after the modified risk product or other tobacco product is prescribed to the first subject or the first subject is otherwise verified as eligible to purchase or use the product.

In some embodiments, the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the product is prescribed by a physician, a nurse, a pharmacist, or an accredited healthcare provider.

In some embodiments, the subject eligibility verification comprises providing a prescription from an accredited healthcare provider, verifying a subject's identity, a minimum age for eligibility, or verification of a prior nicotine replacement therapy.

Once the subject is verified as eligible (e.g., based upon the results of the diagnostic test or prescription by a physician or healthcare provider), the verified subject can be provided with evidence of eligibility for purchase or use of the modified risk product. For example, subject may be provided with an electronic or telephonic verification of a unique subject eligibility card or code identifier, software verification of a unique subject eligibility card or code identifier, electronic fingerprint verification, an activation code, entry into a database, or an electronic dongle, electronic security key fob, or the equivalent.

In some embodiments, components of the subject eligibility verification may be performed by a physician, a nurse, a pharmacist, an accredited healthcare provider, or an employee of a convenience or retail store. In some embodiments, components of the subject eligibility verification can be self-administered.

Referring to FIG. 3B, in some embodiments, the subject eligibility verification includes administering a diagnostic test. For example, the diagnostic test can include collecting samples and measuring nicotine or other by-product of tobacco use, such as cotinine, levels in blood samples, expelled breath samples, saliva samples, hair samples, and in urine samples to verify that the subject's nicotine or nicotine by-product levels are above or consistent with levels expected for a tobacco or nicotine user. As shown in FIG. 3C, a nicotine or cotinine test can determine whether the subject is positive or negative for tobacco. In some embodiments, a cotinine concentration of greater than 7 ng/ml, greater than 8 ng/ml, greater than 10 ng/ml, or greater than 12 ng/ml in a subject's saliva can be used to identify a user of tobacco. Likewise, a cotinine concentration of greater than 35 ng/mL, greater than 40 ng/mL, greater than 42 ng/mL, or greater than 49 ng/mL in a subject's urine can be used to identify a user of tobacco.

Another example of a diagnostic test for subject eligibility verification is a breath carbon monoxide (CO) test. The breath carbon monoxide test can be administered, for example, with a carbon monoxide breath monitor 20 as shown in FIG. 3D. In some embodiments, the monitor can be handheld. The carbon monoxide monitor 20 can include a sensor 22, such as an electrochemical gas sensor, and a mouthpiece 28 for the subject to expel air through. The sensor 22 can be used to detect the carbon monoxide in parts per million (ppm). In some embodiments, a CO concentration of greater than 5 ppm, greater than 6 ppm, greater than 8 ppm, or greater than 10 ppm can be used to identify a user of tobacco, e.g. a user of combustible tobacco. For example, the minimum threshold level can be between 3-5 ppm, between 5-10 ppm, or greater than 1 ppm. In some embodiments, the CO level in a user's blood can be used to determine whether the user has ingested tobacco. The carbon monoxide test can advantageously detect CO when someone ingested tobacco within 10 hours before the test, such as within 8 hours or within 6 hours. Likewise, the carbon monoxide test can detect when someone has ingested tobacco regularly such that CO has built up a reservoir in their blood or lungs. In some embodiments, the carbon monoxide test can be given in the morning (such as within 4 hours of the subject awaking), as regular tobacco users tend to use tobacco within several hours of waking. Further, the carbon monoxide test can be used to determine whether the subject is a light or heavy smoker. For example, a reading of between 6 and 10 ppm can indicate a light user, and a reading of greater than 10 ppm can indicate a heavy user. In some embodiments, eligibility verification can be provided only for heavy users.

Any of the diagnostic tests described herein can also include a mechanism to exclude or select for users who have particular smoking, cardiovascular, or respiratory diseases or conditions, such as asthma or chronic obstructive pulmonary disease (i.e., the eligibility verification can be negative such that the user cannot obtain the modified risk product). For example, the diagnostic test can include a nitric oxide (NO) breath analysis to eliminate or select for these subjects.

It is to be understand that additional diagnostic tests can also be used to determine if the subject is a tobacco user, such as tests for thiocyanate, 4-Aminobiphenyl-hemoglobin adduct, Benzo[a]pyrene-DNA adduct, PAH-albumin adduct, urinary tobacco-specific nitrosoamines, urine hyroxyproline, and/or urine mutagenicity levels in the subject. Exemplary cut-off levels for various diagnostic tests (i.e. a measured level above the cut-off value indicates a tobacco user eligible for use of the modified risk product) are included in FIG. 3E.

In some embodiments, when a diagnostic test is used to determine eligibility verification, the readings can be displayed on the device itself. For example, the specific readings (e.g., ppm of CO) can be indicated on a display of the device, such as the display 24 of device 20 or an indication of passing the cut-off value (e.g., a particular light 26 or the word "pass" on the display 24 of the device 20) can be indicated on the monitor or device. In other embodiments, when a diagnostic test is used, the results can be processed by a third party, e.g., the device or readings from the device can be passed onto a third party to determine whether the subject is eligible for the modified risk product.

In some embodiments, the product is administered by physician, a nurse, a pharmacist, an accredited healthcare provider, or an employee of a convenience or retail store.

In some embodiments, the product is administered by an internet or wireless based application, service or business, or by a call center or phone based application service or business. The use of Skype or other real time phone and internet services makes these verification and prescribing services possible In some embodiments, the risk evaluation and mitigation strategy incorporates a means of subject compliance verification.

In some embodiments, the subject compliance verification comprises collecting and sending samples for analysis, taken before (and/or in some variations, after) being provided a modified risk product, and measuring the difference between samples for nicotine levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As mentioned previously, some aspects of these methods may require physical tests that must be performed to verify subject compliance or REMS validation wherein the subject must present themself to a qualified individual in order for the test to be completed. In some embodiments, the subject compliance verification or REMS validation testing is performed by a physician, a nurse, a pharmacist, a phlebotomist, or an accredited healthcare provider.

In other embodiments, subject compliance verification is performed by an accredited employee of a convenience or retail store, or an employee of an accredited convenience or retail store.

In some embodiments, the risk evaluation and mitigation strategy incorporates a passive means of subject compliance verification.

As previously described, a device that is a component of a modified risk system, may comprise an electronic cigarette, an electronic pipe, an electronic cigar, an electronic water pipe, an electronic vaporizer, and/or a tobacco or nicotine product, for delivering a nicotine-containing vapor, comprising a battery, an atomizer, electronic circuitry, a memory storage device for tracking various aspects of component usage activity, a means of memory transfer, and a charging circuit, along with a charger base station comprising a memory storage device, a means for receiving data from said component device memory storage device and comprising the means to transmit said data to a third party which monitors the device and indirectly, the subject, for compliance to the REMS based on the transmitted data.

The component device would be configured such that activation software acting as a user identification system would be required for recognition of the specific device, keyed to said charger base. This software could be embedded and matched to each component set in a modified risk product, and be capable of interfacing with an external device, wherein said external device comprises; a smart phone, computer, electronic fob, electronic dongle, and a Bluetooth or wireless device, which would need to be within a fixed range for activation and continued use.

Alternatively, the device could be configured to have a fingerprint or lip print reader on the body or mouthpiece that is matched to the first subject.

Alternatively a special ring or wrist band worn on the hand of the first subject or other article of jewelry or clothing could provide a user identification system and be configured to mate with the device, wherein the device will only activate if it is in the immediate proximity of the subject's hand or the subject.

Referring to FIG. 5, in some embodiments, the device itself can include a diagnostic test for verification eligibility. For example, the modified risk product or other tobacco product can include a CO breath analysis sensor directly on the device, such as on the mouthpiece of the modified risk product, that only allows use of the device if the user is verified as a user of tobacco (e.g. has a CO level of above a particular amount as described above, including above average values for a non-tobacco user).

Examples of sensors and sensor technologies that may be used may include electrochemical and Metal oxide semiconductor (MOS) sensors. An electrochemical sensor may produce a current that is related to the target gas concentration around a sensor. For example, an electrochemical cell may be used, to provide a highly accurate and linear output to carbon monoxide concentration, requiring minimal power, and has a long lifetime (e.g., 5 years or greater). MOS (Metal oxide semiconductor) are typically low cost, small size and may provide superior performance. For example, the Figaro TGS5342 electrochemical sensor is 15 mm diameter, 27.9 mm length, however similar sensors may be smaller. In particular, sensors configured to operate as a gating/enabling tool for use of any of the devices (e.g., modified risk products or other tobacco products) described herein may be specifically adapted to sample a patient's breath before they can operate the device. Once the sensor has confirmed that the CO level is above a naïve threshold (e.g., a threshold of CO levels for non-smokers, and/or those who have not used modified risk products or other tobacco products before), the device may be enabled for operation for some amount of time (e.g., seconds, minutes, hours). Other examples of sensors may include SGX sesnortech (E.g., EC4-2000-CO and MICS-4514 MOS sensors), Figaro TGS3870 MOS sensors, and the like.

In any of the prior examples, the devices could be configured with proximity sensors requiring the subject to be within a fixed distance such as 20 feet, or ten feet, or more preferably within five feet or less.

Alternatively, the components could be configured with a programmable code which must be entered periodically for activation. Still further the components could be hard wired with a timing circuit that requires a minimal period of time between uses for activation.

In addition, the device could be configured as shown in FIG. 6 with a base having hardware and software for the transmission of collected data as previously described.

Provided herein is a method of treating a first subject addicted to a tobacco product, the method comprising administering to the first subject who has previously failed nicotine replacement therapy, a modified risk product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by or an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by or an employee of a convenience or retail store.

Provided herein is a method of treating a first subject addicted to a tobacco product, the method comprising administering to the first subject a modified risk product or other tobacco product only after at least one failed attempt by the first subject to quit using such tobacco product.

In some embodiments the modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments the previously failed nicotine replacement therapy comprises abstinence, nicotine gum, nicotine oral spray, nicotine inhaler, nicotine nasal spray, nicotine lozenge, nicotine dermal patch, Bupropion®, Chantix®, or comparable oral nicotine replacement product.

In some embodiments, the product is administered by a physician, a nurse, a pharmacist, or an accredited healthcare provider.

In some embodiments, the product is administered by an employee of a convenience or retail store.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method of treating a first subject addicted to a tobacco product, the method comprising administering a modified risk product or other tobacco product to the first subject only after the modified risk product or other tobacco product is prescribed to the first subject.

In some embodiments, said modified risk product or other tobacco product comprises; an electronic cigarette, an electronic pipe, an electronic cigar, an electronic water pipe, an electronic vaporizer, and/or a tobacco or nicotine product, used in combination with a risk evaluation and mitigation strategy and may involve subject eligibility verification, subject compliance verification to a risk mitigation strategy and overall validation of the success of said risk evaluation and mitigation strategy.

In some embodiments, the modified risk product or other tobacco product is prescribed and administered by a physician, a nurse, a pharmacist, or an accredited healthcare provider.

In some embodiments, the product is administered by an accredited employee of a convenience or retail store, or an employee of an accredited convenience or retail store.

In some embodiments, the product is administered by an internet or wireless based application, service or business.

In some embodiments, the product is administered by a call center or phone based application service or business.

In some embodiments, the subject eligibility verification comprises collecting samples and measuring nicotine levels, nicotine levels, CO levels, or other biomarker levels in blood samples, in expelled breath samples, in saliva samples, in hair samples, and in urine samples to verify that the subject's nicotine or nicotine by-product levels, nicotine levels, CO levels, or other biomarker levels are above or consistent with levels expected for a tobacco or nicotine user.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In some embodiments, the subject compliance verification comprises collecting samples and measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva samples, measuring nicotine levels, nicotine levels, CO levels, or other biomarker levels in hair samples, and measuring nicotine levels, nicotine levels, CO levels, or other biomarker levels in urine samples.

In some embodiments, the subject compliance verification is performed by a physician, a nurse, a pharmacist, or an accredited healthcare provider.

In some embodiments, the subject compliance verification is performed by an employee of a convenience or retail store.

Provided herein is a method for increasing the likelihood that the first subject or a second subject will stop using the tobacco product.

In some embodiments, the subject compliance verification comprises collecting and sending samples for analysis, taken before (and/or in some variations, after) being provided a modified risk product, and measuring the difference between samples for nicotine levels, nicotine levels, CO levels, or other biomarker levels in blood, expelled breath, saliva, hair, and in urine.

In some embodiments, components of the subject compliance verification may be performed by a physician, a nurse, a pharmacist, an accredited healthcare provider, or an employee of a convenience or retail store.

In other embodiments, the compliance verification may comprise measuring maximum plasma concentration (Cmax) of nicotine, compared to a cigarette, the pharmacokinetic profile of the modified risk product or other tobacco product to determine the time required after administration of the product for nicotine to reach maximum plasma concentration (Tmax), compared to a cigarette, or alternatively, to determine the rate-of-increase of nicotine delivery or concentration in the plasma of a subject compared to a cigarette.

In still other embodiments, the compliance verification may comprise measuring relative potential risk of the modified risk product or other tobacco product by comparing the nicotine concentration of the modified risk product or other tobacco product to other nicotine products in the market. Analysis of lab results and statistical analysis of subject outcomes would be performed to provide regular reports to the manufacture(s) and the FDA so that periodic evaluation of reports of patient responses to treatment, medication/devices, and revisions to medication guides, may be reassessed.

As a result of having performed the compliance verification testing, subjects are more likely to be interested in the outcomes and act on those results, including increasing the likelihood that the first subject or a second subject will stop using the tobacco product.

Provided herein is a method for decreasing the likelihood that a second subject not using the tobacco product will start using the tobacco product. FIGS. 4 and 5 are both illustrations of how a second user would be prevented from acquiring and using a modified risk tobacco product, hence, reducing the likelihood of starting to use the tobacco product.

Provided herein is a method for verifying the at least one prior failed attempt to stop using tobacco products prior to the modified risk product or other tobacco product being provided to a first subject.

Provided herein is a method for verifying that a first subject meets at least one eligibility requirement for use of a modified tobacco risk product, as illustrated by FIGS. 3A & 3B.

Provided herein is a method for verifying a subject's eligibility requirement comprising: possession of an eligibility card, meeting qualifications for the eligibility card, possessing a valid verification code, possessing a physician-provided eligibility record, possessing a pharmacist-provided eligibility record, passing a pharmacist-provided eligibility evaluation, as illustrated by FIG. 4.

In some embodiments of a method having an eligibility requirement, the identity verification step comprises at least one of:
evidence of a minimum age requirement,
evidence of a previously failed nicotine replacement therapy, and
evidence of a at least one failed attempt by the patient to quit using such tobacco product,
electronic or telephonic verification of a unique subject eligibility card or code identifier,
software verification of a unique subject eligibility card or code identifier,
electronic fingerprint verification of an eligible subject, an activation code, or
an electronic dongle, electronic security key fob, or equivalent.

Provided herein is a method for verifying a subject's eligibility requirement wherein the verifying step is performed by a physician, a nurse, a pharmacist, or an accredited healthcare provider.

In some embodiments, the verifying a subject's eligibility requirement is performed by an accredited employee of a convenience or retail store, or by an employee of an accredited convenience or retail store.

In some embodiments, the verifying a subject's eligibility requirement is performed by an internet or wireless based application, service or business.

In some embodiments, the verifying a subject's eligibility requirement is performed by an internet or wireless based application, service or business.

Provided herein is a method for providing a prescription for a modified risk product, wherein said prescription is provided by a qualified healthcare provider.

Provided herein is a method of monitoring compliance of a first subject addicted to a tobacco product, and provided with a modified risk product, the method comprising, measuring nicotine levels, nicotine levels, CO levels, or other biomarker levels of a first subject prior to administration of said modified risk product or other tobacco product and routine measurement after administration of said modified risk product, and comparing said prior nicotine levels, nicotine levels, CO levels, or other biomarker levels to anticipated nicotine levels, nicotine levels, CO levels, or other biomarker levels of the first subject after administration of said modified risk product.

In some embodiments the method of monitoring compliance comprises; measuring nicotine levels, nicotine levels, CO levels, or other biomarker levels in blood samples, measuring nicotine levels, nicotine levels, CO levels, or other biomarker levels in expelled breath samples, measuring nicotine levels, nicotine levels, CO levels, or other biomarker levels in saliva or urine samples, as illustrated in FIG. 7, or measuring nicotine levels, nicotine levels, CO levels, or other biomarker levels in hair samples.

Provided herein is a method of monitoring compliance of a first subject addicted to a tobacco product, and provided with a modified risk product, the method comprising, measuring nicotine levels consumed by a first subject prior to administration of said modified risk product or other tobacco product and routine measurement of nicotine levels consumed after administration of said modified risk product, and comparing said prior nicotine levels to anticipated nicotine levels of the first subject after administration of said modified risk product. Numerous methods can be devised as evidence herein, and further illustrated by one example as shown in FIG. 6.

In some embodiments, a method of monitoring comprises; using an electronic signature to track the pattern of use of a vaporizer, electronic cigarette, or other modified risk product or other tobacco product wherein said product transmits a record of use over a given period of time.

In some embodiments, a record of use comprises levels of nicotine consumed, times, and dates it was consumed.

In some embodiments, the record of use is stored to a data storage device and later downloaded for use by a qualified healthcare provider.

In some embodiments, the record of use is transmitted wirelessly to a data storage device and later downloaded for use by a qualified healthcare provider.

In some embodiments, the record of use is stored within the device, and later downloaded for use by a qualified healthcare provider.

Provided herein is a method of monitoring the use of a modified risk product or other tobacco product by a first subject addicted to a tobacco product, the method comprising, requiring an identification recognition system be activated before use of a modified risk product or other tobacco product can take place.

In some embodiments, the identification recognition system comprises, a fingerprint scanner, a lip print scanner, face recognition, a retinal scan, a combination code, an activation code, security key fob, or dongle.

In some embodiments, the identification recognition system comprises an electronic application for a smartphone, laptop, desktop, or tablet computing device, capable of communicating with the modified risk product or other tobacco product by a Bluetooth or wireless communication system.

In some embodiments, the identification recognition system must be within a fixed distance of the modified risk product or other tobacco product for product to continue to work.

In some embodiments, the identification recognition system must be within 20 feet of the modified risk product.

In some embodiments, the identification recognition system must be within 10 feet of the modified risk product.

In some embodiments, the identification recognition system must be within 5 feet of the modified risk product.

Provided herein is a method of risk mitigation wherein the potential risk of misuse or abuse of a modified risk product or other tobacco product may be present and require a distinct form of compliance monitoring.

For example, an addicted subject may continue to use the first tobacco product after being provided the modified risk product, thus increasing the potential risk for one or more tobacco related diseases or exposure to one or more harmful substances.

In some embodiments, monitoring for misuse or abuse of a modified risk product or other tobacco product comprises measuring nicotine levels consumed by a first subject prior to administration of said modified risk product or other tobacco product and routine measurement of nicotine levels consumed after administration of said modified risk product, and comparing said prior nicotine levels to anticipated nicotine levels of the first subject after administration of said modified risk product.

For example, if an investigator suspected that the subject was continuing to use cigarettes after receiving a modified risk product, the results of additional nicotine in the subject's system would be a relatively simple calculation. An example of this calculation could be:

[Nicotine or cotinine from cigarettes]=[amount measured in blood or saliva]−[amount reported as dispensed by modified risk device]. It is understood that a similar calculation could be derived from any comparable nicotine/cotinine test regardless of the testing method, provided testing methods were consistent and/or interchangeable.

In some embodiments, multiple compliance verification and tracking systems could be combined and randomly or non-randomly applied as part of a REMS program. For example, results of a subject's nicotine level, nicotine levels, CO level, or other biomarker level testing could be compared to prior results (FIG. 7), in addition to remotely monitoring transmitted usage patterns of the modified risk product or other tobacco product (FIG. 6). Upon comparison, a skilled health professional could determine if abuse or misuse is potentially occurring.

Provided herein is a method of protecting the public health comprising increasing the likelihood that a first subject or a second subject will stop using a tobacco product by providing a modified risk product or other tobacco product for administration to the first subject addicted to the tobacco product wherein the modified risk product or other tobacco product provides a faster onset of nicotine delivery, or a higher peak level of nicotine delivery.

Provided herein is a method of risk mitigation wherein the potential risk of misuse or abuse of a modified risk product or other tobacco product is ranked or stratified in comparison to other tobacco products.

In some embodiments, the relative potential risk of the modified risk product or other tobacco product is determined by comparing the pharmacokinetic profile of the modified risk product or other tobacco product to nicotine.

In some embodiments the pharmacokinetic profile of the modified risk product or other tobacco product is determined by the maximum plasma concentration (Cmax) of nicotine, compared to a cigarette.

In some embodiments the pharmacokinetic profile of the modified risk product or other tobacco product is determined by the time after administration of the product for nicotine to reach maximum plasma concentration (Tmax), compared to a cigarette.

In some embodiments the pharmacokinetic profile of the modified risk product or other tobacco product is determined by the rate-of-increase of nicotine delivery or concentration in the plasma of a subject compared to a cigarette.

In some embodiments, the relative potential risk of the modified risk product or other tobacco product is determined by comparing the nicotine concentration of the modified risk product or other tobacco product other nicotine products in the market.

In some embodiments, the relative potential risk of the modified risk product or other tobacco product is ranked by ease of access associated with the prescriber/administrator.

In some embodiments, the relative potential risk of the modified risk product or other tobacco product is ranked by ease of access through various distribution channels.

In some embodiments the modified risk product or other tobacco product comprises vaporizing tobacco leaves or finely chopped tobacco below their pyrolytic temperature.

In some embodiments the modified risk product or other tobacco product comprises heating tobacco leaves or finely chopped tobacco below their pyrolytic temperature.

In some embodiments the modified risk product or other tobacco product comprises vaporization of a nicotine salt.

In some embodiments the modified risk product or other tobacco product comprises heating of a nicotine salt below its pyrolytic temperature.

Provided herein is a method of validating the effectiveness of a modified risk product or other tobacco product used with a Risk Evaluation and Mitigation Strategy comprising: collecting and sending a subject's samples taken before (and/or in some variations, after) being provided a modified risk product, for analysis to an accredited testing facility, measuring the difference between samples for nicotine levels, nicotine levels, CO levels, or other biomarker levels in blood, expelled breath, saliva, hair, and/or urine, and performing an appropriate analysis to determine if the modified risk product or other tobacco product met the goals of the Risk Evaluation and Mitigation Strategy.

In some embodiments, components of the validation process may be performed by a physician, a nurse, a pharmacist, an accredited healthcare provider, or an employee of a convenience or retail store or an accredited testing facility.

Provided herein is a method of protecting the public health wherein the provider of a modified risk product is subject to a compliance verification system.

In some embodiments, the provider verification is performed by an independent auditor.

Provided herein is a system for verification, tracking, and reporting use of a modified risk product comprising: an electronic cigarette, an electronic pipe, an electronic cigar, an electronic water pipe, an electronic vaporizer, and a tobacco or nicotine product, comprising a battery, an atomizer, electronic circuitry, a memory storage device for tracking components of usage activity, a means of memory transfer, and a charging circuit, a charger base station comprising a memory storage device, a means for receiving data from said modified risk product memory storage device and transmitting said data to a third party, activation software for recognition of a specific device, keyed to said charger base, capable of interfacing with an external device, wherein said external device comprises; a smart phone, computer, electronic fob, electronic dongle, and a Bluetooth or wireless device.

In some embodiments, the system is used in combination with a risk evaluation and mitigation strategy.

In some embodiments, the system comprises activation means, for recognition and verification of a subject to establish user eligibility prior to use.

In some embodiments, the system comprises activation means, for recognition and verification of a subject to establish user eligibility prior to use.

In some embodiments, the system is used to verify subject compliance for use of a modified risk product. In some embodiments the system comprises a means for validating overall success of the risk mitigation product when used with the risk evaluation and mitigation strategies While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising:
   sampling, via a sensor, a sample of breath of a user of an electronic vaporizer, the sensor disposed on a mouthpiece of the electronic vaporizer;

generating, via the sensor, a current corresponding to a level of carbon monoxide gas in the sample of the breath of the user;

comparing, via electronic circuitry, the corresponding level of the carbon monoxide gas with a threshold to determine whether the user has previously used a tobacco product; and enabling operation, via the electronic circuitry, of the electronic vaporizer based on determining that the corresponding level of the carbon monoxide gas in the sample of the breath of the user exceeds the threshold.

2. The method of claim 1, wherein the threshold is five parts per million of carbon monoxide.

3. The method of claim 1, wherein the threshold is ten parts per million of carbon monoxide.

4. The method of claim 1, wherein the threshold comprises a value indicative of whether the user has consumed the tobacco product within the last twenty-four hours.

5. The method of claim 1, wherein the threshold comprises a value indicative of whether the user has previously consumed combustible tobacco.

6. The method of claim 1, wherein the threshold comprises a value indicative of whether the user has previously consumed tobacco from an electronic cigarette, an electronic pipe, an electronic cigar, an electronic water pipe, or an electronic vaporizer.

7. The method of claim 1, further comprising:

verifying, based on matching a code entered via an electronic dongle or an electronic security key fob, whether the user is eligible to operate the electronic vaporizer, wherein the enabling operation of the electronic vaporizer is also based on the verifying that the user is eligible to operate the electronic vaporizer.

8. An electronic vaporizer comprising:

a sensor configured to sample a user's breath and to generate a current corresponding to a level of carbon monoxide gas in the sample, the sensor disposed on a mouthpiece of the electronic vaporizer; and electronic circuitry configured to perform operations comprising:

comparing the corresponding level of the carbon monoxide gas with a threshold to determine whether the user has previously used a tobacco product; and enabling operation of the electronic vaporizer based on determining that the corresponding level of the carbon monoxide gas in the sample exceeds the threshold.

9. The electronic vaporizer of claim 8, wherein the sensor comprises a carbon monoxide sensor.

10. The electronic vaporizer of claim 9, wherein the threshold is five parts per million of carbon monoxide.

11. The electronic vaporizer of claim 9, wherein the threshold is ten parts per million of carbon monoxide.

12. The electronic vaporizer of claim 8, wherein the threshold comprises a value indicative of whether the user has consumed a tobacco product within the last twenty-four hours.

13. The electronic vaporizer of claim 8, wherein the threshold comprises a value indicative of whether the user has previously consumed combustible tobacco.

14. The electronic vaporizer of claim 8, wherein the threshold comprises a value indicative of whether the user has previously consumed tobacco from an electronic cigarette, an electronic pipe, an electronic cigar, an electronic water pipe, or an electronic vaporizer, or other non-combustion tobacco product.

15. The method of claim 1, wherein the sensor comprises an electrochemical sensor.

16. The method of claim 1, wherein the sensor comprises a metal oxide semiconductor (MOS) sensor.

17. The electronic vaporizer of claim 8, wherein the sensor comprises an electrochemical sensor.

18. The electronic vaporizer of claim 8, wherein the sensor comprises a metal oxide semiconductor (MOS) sensor.

* * * * *